(12) United States Patent
Tipp

(10) Patent No.: US 8,443,466 B2
(45) Date of Patent: May 21, 2013

(54) EAR PROTECTION DEVICE

(75) Inventor: Alan Tipp, Bennington, NE (US)

(73) Assignee: 180s, Inc., Baltimore, MD (US)

( * ) Notice: Subject to any disclaimer, the term of this patent is extended or adjusted under 35 U.S.C. 154(b) by 1316 days.

(21) Appl. No.: 12/018,106

(22) Filed: Jan. 22, 2008

(65) Prior Publication Data

US 2008/0307562 A1  Dec. 18, 2008

Related U.S. Application Data

(60) Provisional application No. 60/886,064, filed on Jan. 22, 2007.

(51) Int. Cl.
*A42B 1/06* (2006.01)
(52) U.S. Cl.
USPC ............................................................ 2/209
(58) Field of Classification Search
USPC .................................. 2/208, 209, 174; 381/370
See application file for complete search history.

(56) References Cited

U.S. PATENT DOCUMENTS

| | | | |
|---|---|---|---|
| 138,894 A | 5/1873 | Isidor | |
| 139,831 A | 6/1873 | Stone | |
| 170,942 A | 12/1875 | Edgar | |
| 183,359 A | 10/1876 | Abbott | |
| 184,006 A | 11/1876 | Edgar | |
| 185,506 A | 12/1876 | Edgar | |
| 188,292 A | 3/1877 | Greenwood | |
| 190,720 A | 5/1877 | Kleinert | |
| 227,364 A | 5/1880 | Kleinert | |
| 315,233 A | 4/1885 | Britton | |
| 358,718 A | 3/1887 | Basch | |
| 359,425 A | 3/1887 | Britton | |
| 359,612 A | 3/1887 | Kleinert | |
| 360,985 A | 4/1887 | Basch | |
| 365,061 A | 6/1887 | Friedman | |
| 375,594 A | 12/1887 | Basch | |
| 381,559 A | 4/1888 | Kleinert et al. | |
| 486,725 A | 11/1892 | Mellor | |
| 503,703 A | 8/1893 | Kleinert | |

(Continued)

FOREIGN PATENT DOCUMENTS

| | | |
|---|---|---|
| CA | 2180036 | 1/1997 |
| CH | 294003 | 1/1954 |

(Continued)

OTHER PUBLICATIONS

Defendant Gordini's First Supplemental and Amended Answers and Objections to Plaintiff's Second Set of Interrogatories (Non-Confidential Version) from *180s, Inc. and 180s, LLC v. Gordini U.S.A., Inc.* (Case 1:08-cv-00177-JFM), 29 pages, dated Feb. 4, 2009.

(Continued)

*Primary Examiner* — Shelley Self
*Assistant Examiner* — Andrew Sutton

(57) ABSTRACT

Various embodiments of ear protection devices are disclosed. In one embodiment, an ear protection device can include a band and ear frame portions. The ear frame portions can include several components, some of which are configured to move relative to each other. The ear frame portions are coupled to the band portion. The band portion is configured to be disposed around the back of a user's head and/or neck. In other embodiments, the frame and fabric components can vary.

10 Claims, 31 Drawing Sheets

U.S. PATENT DOCUMENTS

| | | | |
|---|---|---|---|
| 516,135 A | 3/1894 | Thamm | |
| 529,176 A | 11/1894 | Kleinert | |
| 548,738 A | 10/1895 | Ballard | |
| 636,087 A * | 10/1899 | Callahan | 310/257 |
| 758,680 A | 5/1904 | Otte | |
| 804,731 A | 11/1905 | Keller | |
| 836,087 A | 11/1906 | Callahan | |
| 869,741 A | 10/1907 | Seitzman | |
| 932,487 A | 8/1909 | Melio | |
| 953,623 A | 3/1910 | Keller | |
| 1,149,806 A | 8/1915 | Basch | |
| 1,167,368 A | 1/1916 | Adams-Randall | |
| 1,179,473 A | 4/1916 | Taylor | |
| 1,274,842 A | 8/1918 | Basch | |
| 1,326,875 A | 12/1919 | Miller | |
| 1,395,864 A | 11/1921 | Pape | |
| 1,398,958 A | 12/1921 | Basch | |
| 1,438,171 A | 12/1922 | Delson | |
| 1,567,105 A | 12/1925 | Bohlman | |
| 1,577,183 A | 3/1926 | Dowiarz | |
| 1,628,483 A | 5/1927 | Wiegand et al. | |
| 1,873,864 A | 8/1932 | Ely | |
| 1,945,110 A | 1/1934 | Gordon | |
| 1,988,880 A | 1/1935 | Strouse | |
| 2,070,216 A | 2/1937 | Rosenberg | |
| 2,120,189 A | 6/1938 | Reinemer | |
| 2,149,383 A | 3/1939 | Bean | |
| 2,184,996 A | 12/1939 | Jacobs | |
| 2,216,954 A | 10/1940 | McDonough | |
| 2,241,736 A | 5/1941 | Reinemer | |
| 2,246,031 A | 6/1941 | Baritz et al. | |
| 2,314,782 A | 3/1943 | Goretsky | |
| 2,333,392 A | 11/1943 | Rosenzweig | |
| 2,378,398 A | 6/1945 | Fiedler | |
| 2,405,326 A | 8/1946 | Plotsky | |
| 2,420,245 A | 5/1947 | Hurst | |
| 2,437,049 A | 3/1948 | Salisbury et al. | |
| 2,439,289 A | 4/1948 | Fanslow | |
| 2,447,078 A | 8/1948 | Maxant | |
| 2,464,331 A | 3/1949 | Mason | |
| 2,532,852 A | 12/1950 | Oaks | |
| 2,572,746 A | 10/1951 | Mougel | |
| 2,582,907 A | 1/1952 | Kaufmann | |
| 2,586,644 A | 2/1952 | Gilbert | |
| 2,609,544 A | 9/1952 | Berg | |
| 2,615,169 A | 10/1952 | Maxant | |
| 2,651,046 A | 9/1953 | Berg | |
| 2,671,221 A | 3/1954 | Triplett | |
| 2,678,999 A | 5/1954 | Norris | |
| 2,717,930 A | 9/1955 | Hintz | |
| 2,738,514 A | 3/1956 | Gondell | |
| 2,776,436 A | 1/1957 | Berg | |
| 2,782,423 A | 2/1957 | Simon et al. | |
| 2,858,544 A | 11/1958 | Roth | |
| 2,899,683 A | 8/1959 | Wadsworth et al. | |
| 2,946,860 A | 7/1960 | Jansen et al. | |
| 3,087,028 A | 4/1963 | Bonnin | |
| 3,104,398 A | 9/1963 | Palmaer | |
| 3,112,493 A | 12/1963 | Greenberg | |
| 3,119,119 A | 1/1964 | Millinger et al. | |
| 3,119,904 A | 1/1964 | Anson | |
| 3,156,923 A | 11/1964 | Timm | |
| 3,235,882 A | 2/1966 | Coleman | |
| 3,249,949 A | 5/1966 | Rosenberg et al. | |
| 3,308,480 A | 3/1967 | Elder | |
| 3,311,713 A | 3/1967 | Knuebel | |
| 3,440,663 A | 4/1969 | Beguin | |
| 3,447,160 A | 6/1969 | Teder | |
| 3,505,684 A * | 4/1970 | Hutchinson et al. | 2/209 |
| 3,509,580 A | 5/1970 | Rubenstein et al. | |
| 3,686,691 A * | 8/1972 | Anderson | 2/209 |
| 3,721,993 A | 3/1973 | Lonnstedt | |
| 3,728,741 A | 4/1973 | Lepor | |
| 3,787,899 A | 1/1974 | Krawagna | |
| 3,815,155 A | 6/1974 | Davison et al. | |
| 3,841,325 A | 10/1974 | Pickard | |
| 3,944,018 A | 3/1976 | Satory | |
| 4,048,453 A | 9/1977 | Seidel | |
| 4,133,053 A | 1/1979 | Lundin | |
| 4,277,847 A | 7/1981 | Florio | |
| 4,349,081 A | 9/1982 | Pepple | |
| D266,417 S | 10/1982 | Perez | |
| 4,391,000 A | 7/1983 | Lonnstedt | |
| 4,404,434 A | 9/1983 | Pelt et al. | |
| 4,409,442 A | 10/1983 | Kamimura | |
| 4,445,005 A | 4/1984 | Furuhashi | |
| 4,455,457 A | 6/1984 | Akira | |
| 4,463,223 A | 7/1984 | Yamanoi et al. | |
| 4,471,496 A | 9/1984 | Gardner, Jr. et al. | |
| 4,486,903 A | 12/1984 | Krystal | |
| 4,499,593 A | 2/1985 | Antle | |
| 4,516,274 A | 5/1985 | Buckland | |
| 4,542,803 A | 9/1985 | Houng | |
| 4,546,215 A | 10/1985 | Ferraro | |
| 4,571,746 A | 2/1986 | Gorike | |
| 4,609,786 A | 9/1986 | Omoto et al. | |
| 4,615,185 A | 10/1986 | Bollinger | |
| 4,633,530 A | 1/1987 | Satterfield | |
| 4,654,898 A | 4/1987 | Ishikawa | |
| 4,660,229 A | 4/1987 | Harris | |
| 4,669,129 A | 6/1987 | Chance | |
| 4,670,911 A | 6/1987 | Dunford | |
| 4,682,374 A | 7/1987 | Geiser | |
| 4,713,843 A | 12/1987 | Duncan | |
| 4,727,599 A | 2/1988 | Rappaport et al. | |
| 4,747,145 A | 5/1988 | Wiegel | |
| 4,776,042 A | 10/1988 | Hanson et al. | |
| 4,776,044 A | 10/1988 | Makins | |
| 4,783,822 A | 11/1988 | Toole et al. | |
| 4,791,684 A | 12/1988 | Schwartz | |
| 4,796,307 A | 1/1989 | Vantine | |
| 4,802,245 A | 2/1989 | Miano | |
| 4,805,239 A | 2/1989 | Ciago | |
| D301,477 S | 6/1989 | Storyk | |
| 4,845,751 A | 7/1989 | Schwab | |
| 4,850,055 A | 7/1989 | Hwang | |
| 4,858,248 A | 8/1989 | Goldsmith et al. | |
| 4,864,619 A | 9/1989 | Spates | |
| 4,872,219 A | 10/1989 | Duncan | |
| 4,907,266 A | 3/1990 | Chen | |
| 4,918,757 A | 4/1990 | Janssen et al. | |
| 4,930,148 A | 5/1990 | Lee | |
| 4,969,069 A | 11/1990 | Eichost | |
| 4,982,451 A | 1/1991 | Graham | |
| 5,003,589 A | 3/1991 | Chen | |
| 5,033,094 A | 7/1991 | Hung | |
| 5,035,005 A | 7/1991 | Hung | |
| 5,038,412 A | 8/1991 | Cionni | |
| 5,046,192 A | 9/1991 | Ryder | |
| 5,052,194 A | 10/1991 | Jarus | |
| 5,056,161 A | 10/1991 | Breen | |
| 5,086,789 A | 2/1992 | Tichy | |
| 5,095,382 A | 3/1992 | Abe | |
| 5,113,428 A | 5/1992 | Fitzgerald | |
| 5,117,464 A | 5/1992 | Jones et al. | |
| 5,117,465 A | 5/1992 | MacDonald | |
| 5,164,987 A | 11/1992 | Raven | |
| 5,201,856 A | 4/1993 | Edwards | |
| 5,257,420 A | 11/1993 | Byrne, Jr. | |
| 5,265,165 A | 11/1993 | Rauch | |
| 5,285,530 A | 2/1994 | Nardone, Jr | |
| 5,293,647 A * | 3/1994 | Mirmilshteyn et al. | 2/209 |
| D346,380 S | 4/1994 | Fitzgerald | |
| 5,303,426 A | 4/1994 | Jones | |
| 5,327,178 A | 7/1994 | McManigal | |
| 5,339,467 A | 8/1994 | Brinkley | |
| 5,357,585 A | 10/1994 | Kumar | |
| 5,410,735 A | 4/1995 | Borchardt et al. | |
| 5,509,146 A | 4/1996 | Bryerton, Sr. | |
| 5,528,774 A | 6/1996 | Sanders | |
| 5,545,859 A | 8/1996 | Ullrich | |
| 5,551,089 A | 9/1996 | Whidden | |
| 5,551,090 A | 9/1996 | Thompson | |
| D375,825 S | 11/1996 | Whidden | |
| 5,617,589 A | 4/1997 | Lacore et al. | |
| 5,625,903 A | 5/1997 | Schultz et al. | |
| 5,673,438 A | 10/1997 | Lambert | |

| | | |
|---|---|---|
| 5,691,515 A | 11/1997 | Landis |
| 5,708,725 A | 1/1998 | Ito |
| D390,564 S | 2/1998 | Savona |
| 5,718,001 A | 2/1998 | Wright |
| 5,721,775 A | 2/1998 | Leifer |
| 5,724,119 A | 3/1998 | Leight |
| 5,749,099 A | 5/1998 | Voorhees |
| 5,793,878 A | 8/1998 | Chang |
| 5,821,468 A | 10/1998 | Urella et al. |
| 5,835,609 A | 11/1998 | LeGette et al. |
| 5,860,166 A | 1/1999 | Ritts |
| 5,881,390 A | 3/1999 | Young |
| 5,887,286 A | 3/1999 | Waldron |
| 5,898,945 A | 5/1999 | Weiser |
| 5,943,703 A | 8/1999 | Avila, Jr. |
| 5,951,141 A | 9/1999 | Bradley |
| 5,953,434 A | 9/1999 | Boyden |
| 6,016,574 A | 1/2000 | Chen |
| 6,029,282 A | 2/2000 | Buschman |
| 6,055,672 A | 5/2000 | Natvig |
| 6,065,157 A | 5/2000 | Felman |
| 6,095,146 A | 8/2000 | Knauer et al. |
| 6,104,824 A | 8/2000 | Ito |
| 6,131,204 A | 10/2000 | Otey |
| 6,148,446 A | 11/2000 | Leight |
| 6,212,282 B1 | 4/2001 | Mershon |
| 6,237,157 B1 | 5/2001 | Lobbins |
| 6,332,223 B1 | 12/2001 | LeGette et al. |
| 6,369,958 B1 | 4/2002 | Himmele |
| 6,377,697 B1 | 4/2002 | Cheng |
| 6,392,196 B1 | 5/2002 | Lin |
| 6,406,811 B1 | 6/2002 | Hall et al. |
| 6,499,146 B2 | 12/2002 | Bavetta et al. |
| 6,502,247 B2 | 1/2003 | LeGette et al. |
| 6,502,248 B2 | 1/2003 | LeGette et al. |
| D473,539 S | 4/2003 | O'Leary |
| 6,580,800 B1 | 6/2003 | Yamasaki et al. |
| 6,678,897 B2 * | 1/2004 | Lindgren .......................... 2/209 |
| 6,735,784 B2 | 5/2004 | Isom et al. |
| 6,744,901 B2 | 6/2004 | Ito et al. |
| 6,873,862 B2 | 3/2005 | Reshefsky |
| 6,880,174 B2 | 4/2005 | Prokop |
| 6,888,950 B2 | 5/2005 | Siskin et al. |
| 6,918,678 B2 | 7/2005 | McClanahan |
| 6,920,645 B2 | 7/2005 | LeGette et al. |
| 6,965,681 B2 | 11/2005 | Almqvist |
| 6,978,483 B2 | 12/2005 | Isom et al. |
| 6,980,165 B2 | 12/2005 | Yuasa et al. |
| 7,020,902 B1 | 4/2006 | Tyler |
| 7,024,013 B1 | 4/2006 | Van Dam |
| 7,072,483 B2 | 7/2006 | Lenhard-Backhaus |
| 7,114,823 B2 | 10/2006 | McCullough et al. |
| 7,165,272 B2 | 1/2007 | Hudson et al. |
| D541,482 S | 4/2007 | LeGette et al. |
| 7,210,173 B2 | 5/2007 | Bavetta et |
| 7,222,373 B2 | 5/2007 | Healy et al. |
| D545,001 S | 6/2007 | LeGette et al. |
| 7,318,654 B2 | 1/2008 | McClanahan |
| 7,377,666 B1 | 5/2008 | Tyler |
| 7,424,125 B2 | 9/2008 | Amae et al. |
| 7,548,617 B2 | 6/2009 | Yuen |
| 2001/0017925 A1 | 8/2001 | Ceravolo |
| 2002/0172390 A1 | 11/2002 | Roberts |
| 2003/0037366 A1 | 2/2003 | Lindgren |
| 2004/0252487 A1 | 12/2004 | McCullough et al. |
| 2005/0028250 A1 | 2/2005 | Zaic |
| 2005/0034216 A1 | 2/2005 | LeGette et al. |
| 2005/0034218 A1 * | 2/2005 | Le Gette et al. .................. 2/209 |
| 2005/0036643 A1 | 2/2005 | LeGette et al. |
| 2005/0100184 A1 | 5/2005 | Siskin et al. |
| 2005/0246815 A1 | 11/2005 | LeGette et al. |
| 2005/0283882 A1 * | 12/2005 | Berger et al. ..................... 2/209 |
| 2006/0000006 A1 | 1/2006 | Gellis et al. |
| 2006/0206983 A1 | 9/2006 | Isom et al. |
| 2007/0107110 A1 | 5/2007 | LeGette et al. |
| 2007/0154029 A1 | 7/2007 | Werner |
| 2007/0160249 A1 | 7/2007 | LeGette et al. |
| 2007/0199133 A1 | 8/2007 | Bavetta et al. |
| 2007/0220657 A1 | 9/2007 | LeGette et al. |
| 2007/0226876 A1 | 10/2007 | Foust et al. |
| 2008/0044052 A1 | 2/2008 | Whipple |
| 2008/0141439 A1 | 6/2008 | Healy et al. |
| 2008/0181429 A1 | 7/2008 | Fried |
| 2008/0216214 A1 | 9/2008 | Dolby |
| 2008/0279403 A1 | 11/2008 | Pedersen et al. |
| 2008/0307563 A1 | 12/2008 | LeGette et al. |
| 2008/0307564 A1 | 12/2008 | LeGette et al. |
| 2008/0307565 A1 | 12/2008 | LeGette et al. |
| 2009/0013447 A1 | 1/2009 | Drosihn |
| 2009/0013448 A1 | 1/2009 | Drosihn |
| 2009/0154740 A1 | 6/2009 | Regen et al. |
| 2009/0196453 A1 | 8/2009 | Amae et al. |
| 2009/0205110 A1 | 8/2009 | Chiang |
| 2010/0175165 A1 | 7/2010 | Le Gette |

FOREIGN PATENT DOCUMENTS

| | | |
|---|---|---|
| CH | 662052 | 9/1987 |
| CN | 2291138 | 9/1998 |
| CN | 2353337 Y | 12/1999 |
| DE | 483279 | 9/1929 |
| DE | 641554 | 2/1937 |
| DE | 2516709 A1 | 10/1976 |
| DE | 3231218 A1 | 2/1984 |
| DE | 4422767 A1 | 1/1996 |
| DE | 29800973 U1 | 4/1998 |
| DE | 29812652 U1 | 3/1999 |
| DE | 20003363 U1 | 8/2000 |
| EP | 126690 A1 | 11/1984 |
| EP | 0745364 | 8/2002 |
| FR | 1353524 | 1/1963 |
| FR | 2536253 A1 | 11/1982 |
| FR | 2538204 A1 | 12/1982 |
| FR | 2532838 A1 | 9/1983 |
| GB | 1327614 | 8/1973 |
| GB | 2059206 A | 4/1981 |
| GB | 2062478 | 5/1981 |
| GB | 2226931 A | 7/1990 |
| GB | 2290696 A | 1/1996 |
| GB | 2320885 | 8/1998 |
| GB | 2339642 | 2/2000 |
| JP | 4875626 | 9/1973 |
| JP | 53143627 | 11/1978 |
| JP | 54-168912 U | 11/1979 |
| JP | 56-146719 U | 11/1981 |
| JP | 56-152479 | 11/1981 |
| JP | 56-164218 U | 12/1981 |
| JP | 5711884 | 1/1982 |
| JP | 6029141 | 2/1982 |
| JP | 57205216 | 12/1982 |
| JP | 5815618 | 1/1983 |
| JP | 58-104076 | 7/1983 |
| JP | 58137289 U | 8/1983 |
| JP | 58137289 U | 9/1983 |
| JP | 58138484 | 9/1983 |
| JP | 58154191 U | 10/1983 |
| JP | 58-182594 U | 12/1983 |
| JP | 59129815 | 8/1984 |
| JP | 60244188 | 12/1985 |
| JP | 61-42186 | 3/1986 |
| JP | 623526 | 1/1987 |
| JP | 62-21016 | 2/1987 |
| JP | 63-20232 | 6/1988 |
| JP | 1068506 A | 3/1989 |
| JP | 1068508 A | 3/1989 |
| JP | 1-125319 | 8/1989 |
| JP | 5-207581 | 8/1993 |
| JP | 641720 | 6/1994 |
| JP | 6-351090 | 12/1994 |
| JP | 07-213403 | 8/1995 |
| JP | 10-79994 | 3/1998 |
| JP | 10085251 | 7/1998 |
| JP | 3053142 U | 10/1998 |
| JP | 11-089699 | 4/1999 |
| JP | 11229223 | 8/1999 |
| JP | 10257581 | 8/2000 |
| JP | 3082758 | 12/2001 |
| JP | 200211036 | 1/2002 |
| KR | 200226271 | 3/2001 |

| | | |
|---|---|---|
| KR | 200314976 | 6/2003 |
| KR | 300336877 | 11/2003 |
| KR | 20357405 | 7/2004 |
| KR | 20357406 | 7/2004 |
| KR | 100703878 | 4/2007 |
| SE | 452237 B | 11/1987 |
| WO | 9217079 A1 | 10/1992 |
| WO | 94/02043 A1 | 2/1994 |
| WO | 9409734 A1 | 5/1994 |
| WO | 9748296 A1 | 12/1997 |
| WO | 9807062 A1 | 2/1998 |
| WO | 9831314 A1 | 7/1998 |
| WO | 0176402 A1 | 10/2001 |
| WO | 02083044 A1 | 10/2002 |
| WO | 03086124 A1 | 10/2003 |
| WO | 2010/017359 A1 | 2/2010 |

OTHER PUBLICATIONS 1999-2000 Catalog "Accessory Goods"—Nitty Company, Ltd. 4 pgs.
Chicago Tribune article entitled "Winter From Head to Toe Lend an Ear to the Tale of This Intrepid Inventor," by Sid Moody, Feb. 16, 1988, 4 pgs.

"History of the United States Patent Office—The Patent Office Pony—A History of the Early Patent Office," by Kenneth W. Dobyns, 1994, [Introductory Material—3 pgs; Chapter 29—4 pgs; and Sources and Annotations—40 pgs.]
2003 Catalog, "Join the Polar Fusion Revolution; Revolutionary Ear Warmers," Polar Fusion LLC.—2 pgs.
Nitty Company Ltd. Winter '89-'90 catalog, 6 pages.
Nitty Company Ltd., Winter '90-'91 catalog, 4 pages.
"Hearmuffs" from http://www.hearmuff.com/goods.htm, 2003, 2 pgs.
"Hearmuffs" from http://www.hearmuff.com/about.htm, 2003, 3 pgs.
Opinion from the District Court of Maryland in *180s, Inc. and 180s, LLC* v. *Gordini U.S.A., Inc.* (Case 1:08-cv-00177-JFM), 23 pages, dated Mar. 30, 2010.
International Search Report for PCT/US08/51732, 3 pages, dated Jul. 30, 2008.
"Hearmuff: Fleece headwear with internal stereo headphones" from http://www.hearmuff.com/index.htm, 2003, 1 page.

\* cited by examiner

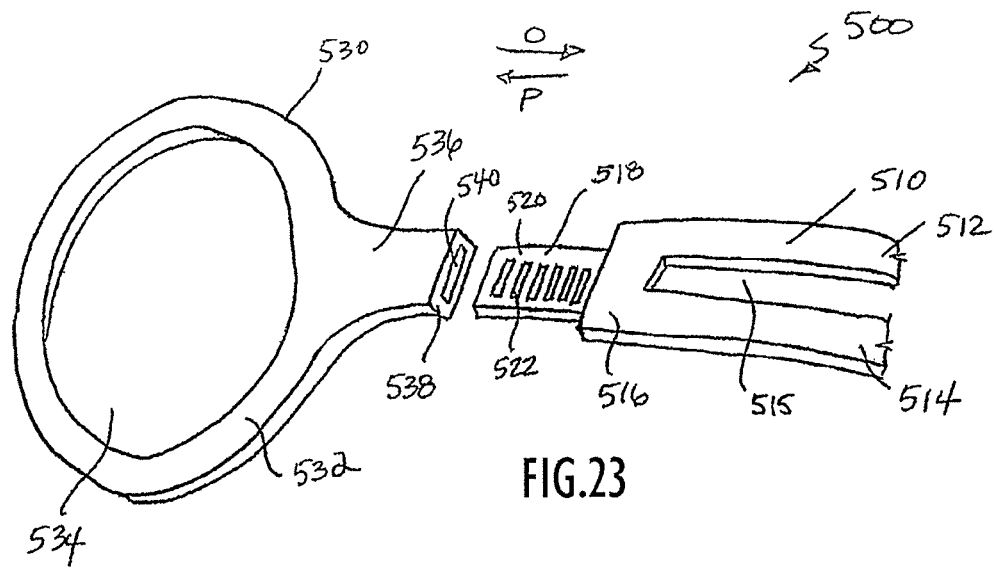
FIG.23
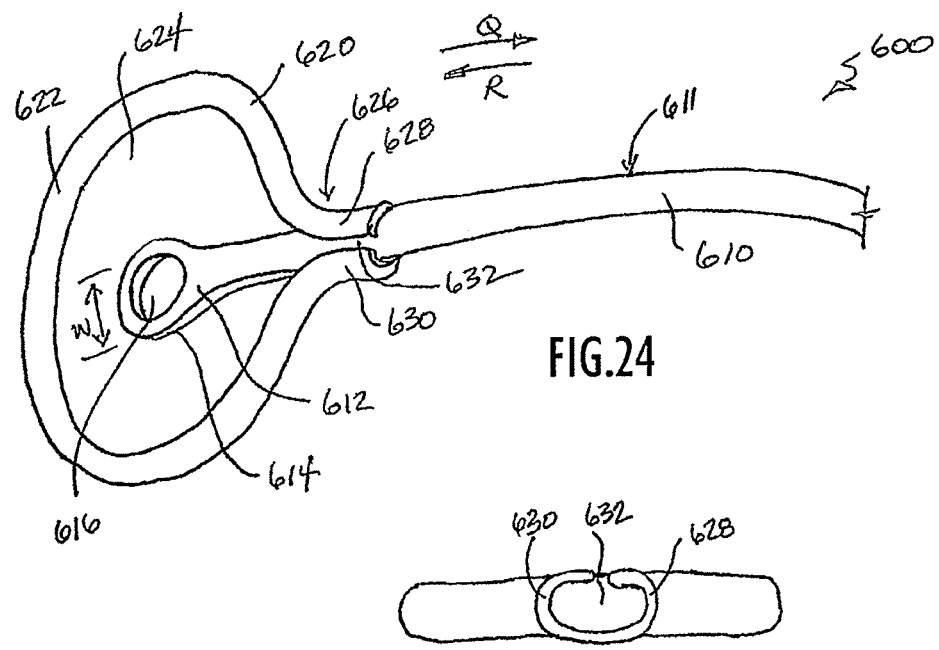
FIG.24
FIG.25

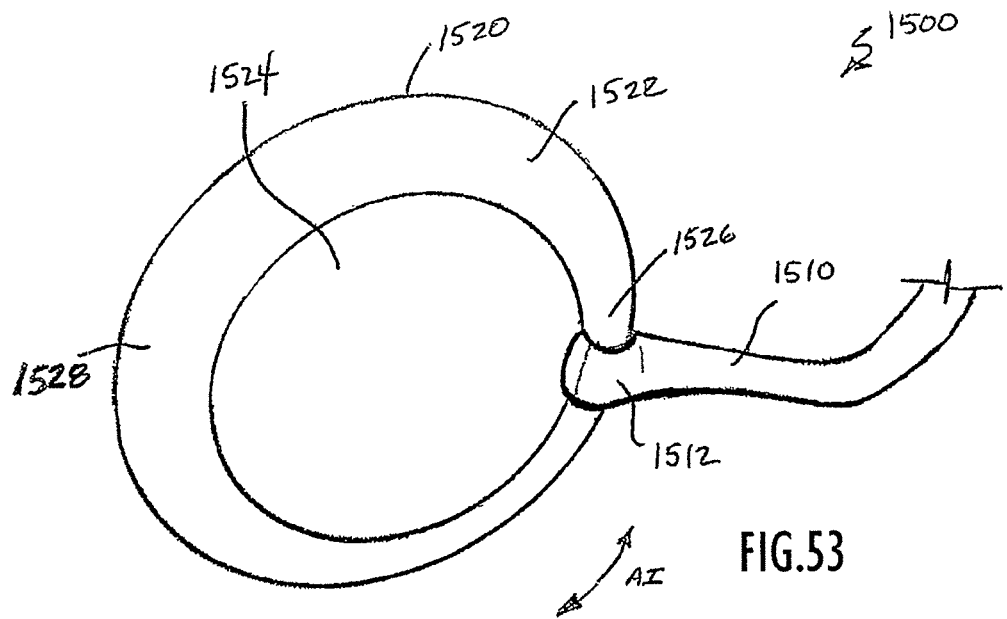
FIG.53
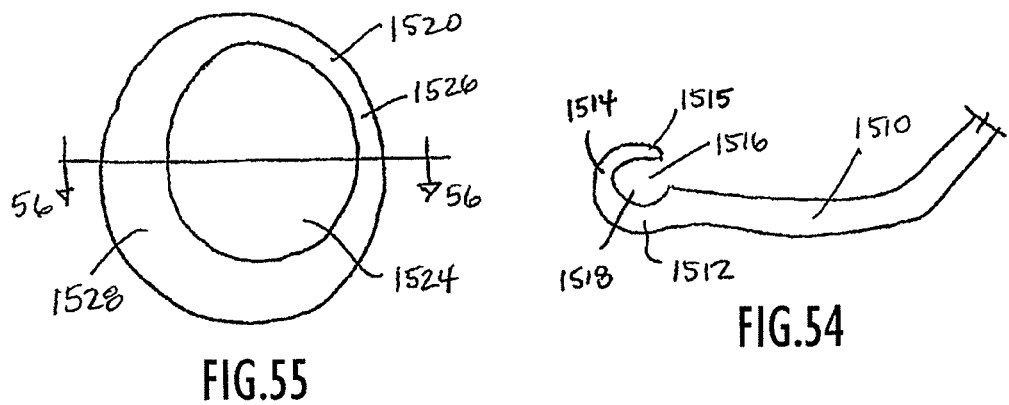
FIG.55
FIG.54
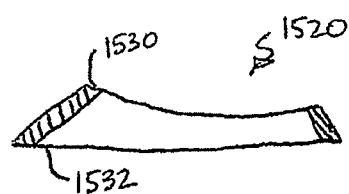
FIG.56
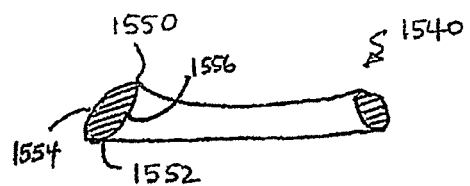
FIG.57

EAR PROTECTION DEVICE

CROSS-REFERENCE TO RELATED APPLICATIONS

This application claims priority to U.S. Provisional Patent Application Ser. No. 60/886,064, entitled "Ear Protection Device," filed Jan. 22, 2007, the disclosure of which is incorporated herein by reference in its entirety.

BACKGROUND OF THE INVENTION

This invention relates generally to ear protection devices. More specifically, the present invention relates to ear protection devices and method for making ear protection devices.

SUMMARY OF THE INVENTION

In one embodiment, an ear protection device includes a frame and a fabric shell. The frame includes several components, some of which move relative to each other. In other embodiments, the frame and fabric components can vary.

BRIEF DESCRIPTION OF THE DRAWINGS

FIG. 23 is an exploded partial outer side view of some components of an alternative embodiment of a frame according to the invention.

FIG. 24 is an exploded partial outer side view of some components of an alternative embodiment of a frame according to the invention.

FIG. 25 is an end view of the ear frame member of the frame illustrated in FIG. 24.

FIG. 53 is a side view of an alternative embodiment of a portion of an ear protection device according to the invention.

FIG. 54 is a top view of a portion of the band of the ear protection device illustrated in FIG. 53.

FIG. 55 is a side view of the ear frame member of the ear protection device illustrated in FIG. 53.

FIG. 56 is a cross-sectional top view of the ear frame member illustrated in FIG. 55.

FIG. 57 is a cross-sectional top view of an alternative embodiment of an ear frame member according to the invention.

DETAILED DESCRIPTION

Figure 1:
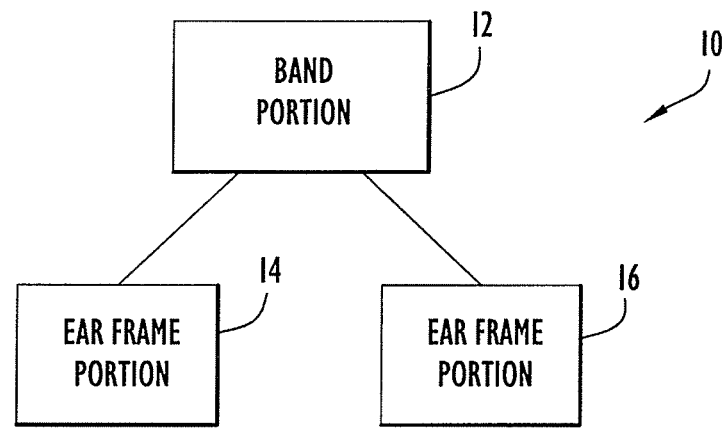
FIG. 1 is a block diagram of an embodiment of an ear protection device according to the invention.

A block diagram of an ear protection device according to an embodiment of the invention is illustrated in FIG. 1. The ear protection device 10 includes a band portion 12 and ear frame portions 14 and 16. The ear frame portions 14 and 16 are coupled to the band portion 12. The band portion 12 is configured to be disposed around the back of a user's head and/or neck. The band portion 12 is constructed, in terms of materials used and dimensions, to provide force on the ear frame portions 14 and 16 to direct them toward each other, thereby applying pressure and a clamping force on the user's head. The forces are used to retain the ear protection device 10 in engagement with the user's head. In various embodiments, the band portion and the ear frame portions can have many configurations. Several exemplary embodiments are disclosed herein.

Figure 2:
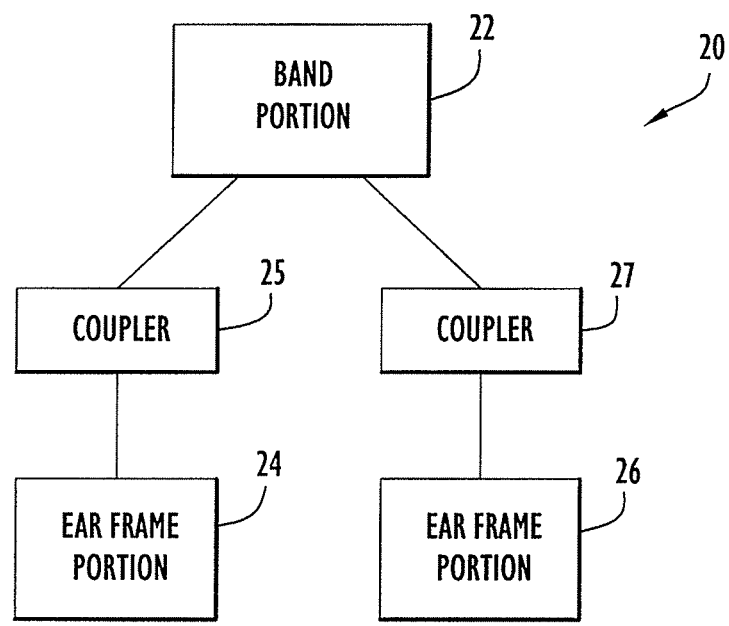
FIG. 2 is a block diagram of an alternative embodiment of an ear protection device according to the invention.

A block diagram of an alternative embodiment of an ear protection device is illustrated in FIG. 2. Ear protection device 20 includes a band portion 22 and ear frame portions 24 and 26. In this embodiment, ear protection device 20 includes couplers 25 and 27. Coupler 25 couples ear frame portion 24 to the band portion 22. Similarly, coupler 27 couples ear frame portion 26 to the band portion 22.

In one embodiment, the couplers 25 and 27 can be any conventional connecting device, such as a rivet or bolt. Alternatively, the couplers 25 and 27 can be formed with either the ear frame portions or the band portion and be slidably engageable with the other of the ear frame portions or the band portion.

Figure 3:
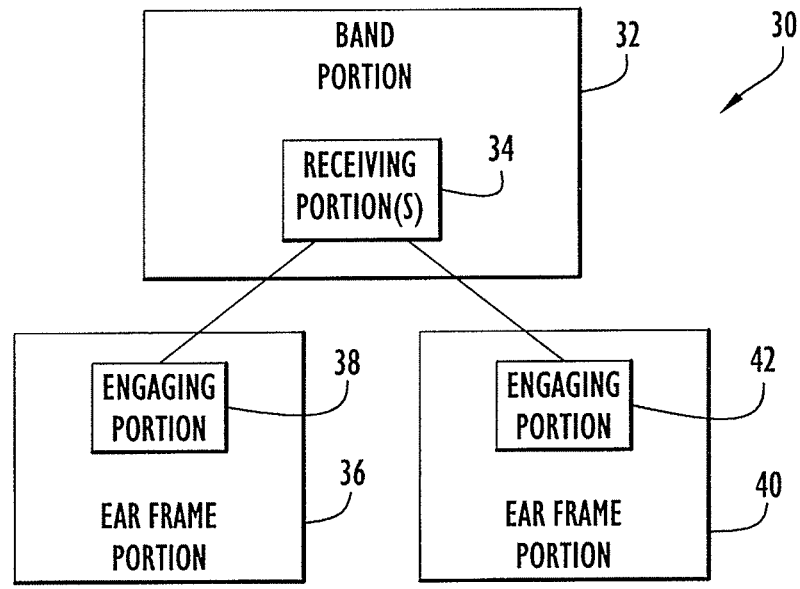
FIG. 3 is a block diagram of an alternative embodiment of an ear protection device according to the invention.

A block diagram of an alternative embodiment of an ear protection device is illustrated in FIG. 3. Ear protection device 30 includes a band portion 32 and ear frame portions 36 and 40. Ear frame portion 36 includes an engaging portion 38. Engaging portion 38 can be a protrusion that is integrally formed with the ear frame portion 36 or a separate connector, such as a rivet, that is inserted through an opening on the ear frame portion 36. Similarly, ear frame portion 40 includes an engaging portion 42.

The band portion 32 includes one or more receiving portions 34 that receive one or both of the engaging portions 38 and 42. In one embodiment, the receiving portion 34 can be a slot through which an engaging portion can be inserted. The engaging portion and the receiving portion couple an ear frame portion and the band portion together for movement relative to each other.

Figure 4:
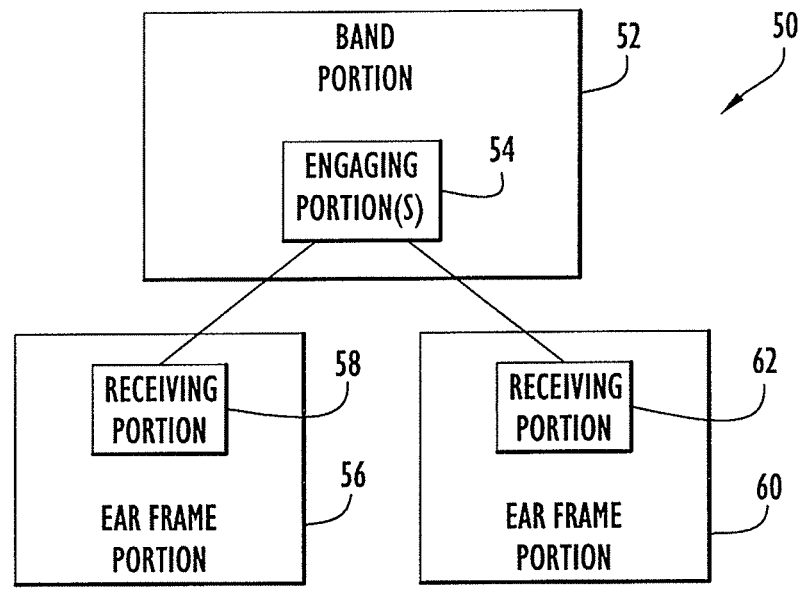
FIG. 4 is a block diagram of an alternative embodiment of an ear protection device according to the invention.

A block diagram of an alternative embodiment of an ear protection device is illustrated in FIG. 4. Ear protection device 50 includes a band portion 52 and ear frame portions 56 and 60. Ear frame portion 56 includes a receiving portion 58 and ear frame portion 60 includes a receiving portion 62. The band portion 52 includes multiple engaging portions 54, each of which is in communication with a corresponding receiving portion.

Figure 5A:
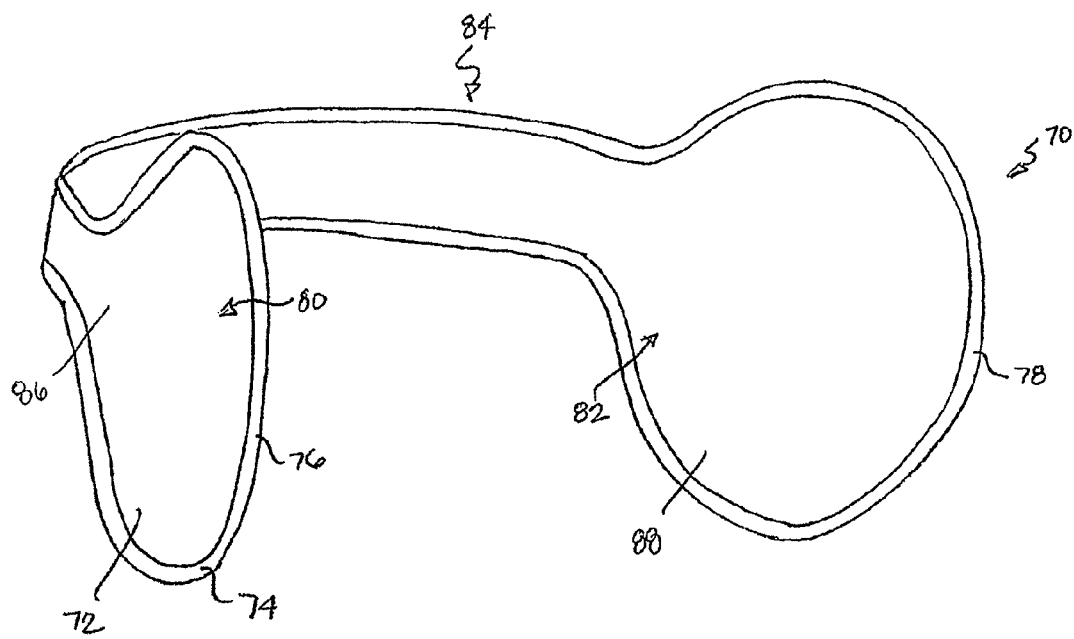
FIG. 5A is a front perspective view of an embodiment of an ear protection device according to the invention.
Figure 6:
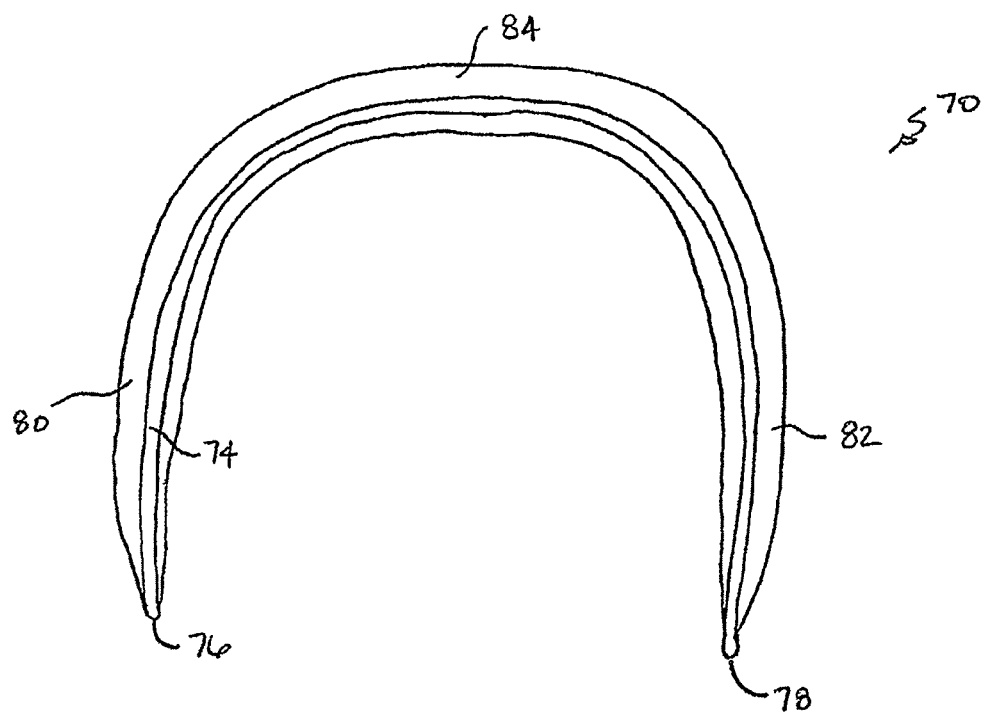
FIG. 6 is a top view of the ear protection device illustrated in FIG. 5A.

A perspective view of an ear protection device according to the invention is illustrated in FIGS. 5A and 6. Ear protection device 70 includes a shell 82 that is formed using one or more pieces of fabric. In this embodiment, the shell 82 includes an outer membrane 86 and an inner membrane 88. The outer membrane 86 and the inner membrane 88 are coupled along their perimeters by a seam that also couples a binding 74 around the perimeters.

The ear protection device 70 has ends 76 and 78 that are formed by ear frame portions 80 and 82. The ear protection device 70 includes a middle portion 84 that is disposed between the ear frame portions 80 and 82.

A frame (not illustrated in FIGS. 5A and 6) is disposed within the shell 70. In one implementation, the ear frame members can be moved relative to the middle portion so that the length of the frame of the ear protection device can be adjusted.

Figure 5B:
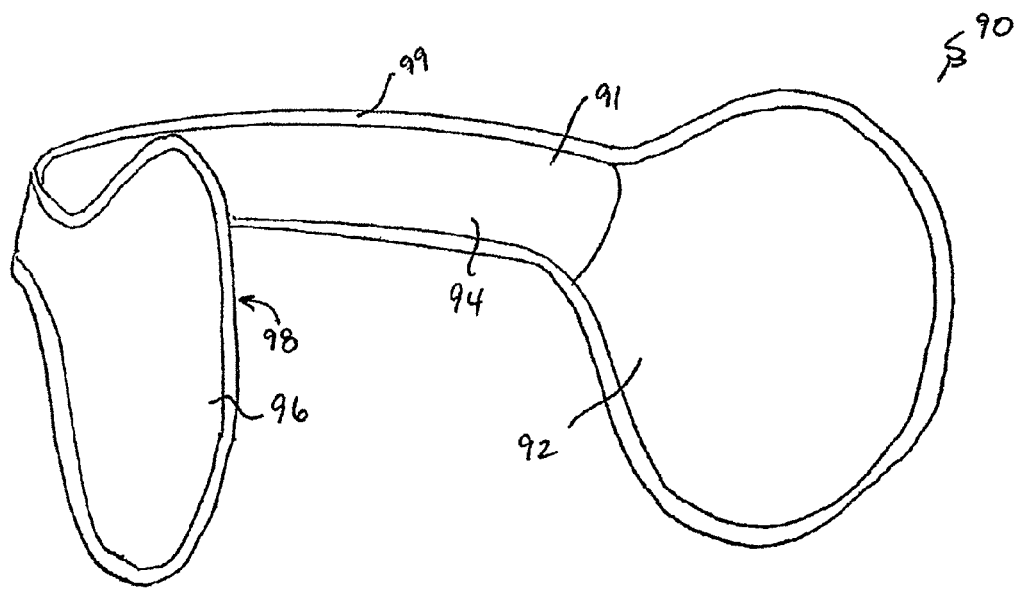
FIG. 5B is a front perspective view of an alternative embodiment of an ear protection device according to the invention.

In an alternative embodiment illustrated in FIG. 5B, the shell 90 is formed using multiple pieces of fabric. In this implementation, the shell 91 includes a first ear portion 92, a second ear portion (98—not shown) opposite the first ear portion, a middle portion 94 and an outer portion 96. A binding 99 is provided around the perimeter of the portions and thereby couples them together.

Figure 7:
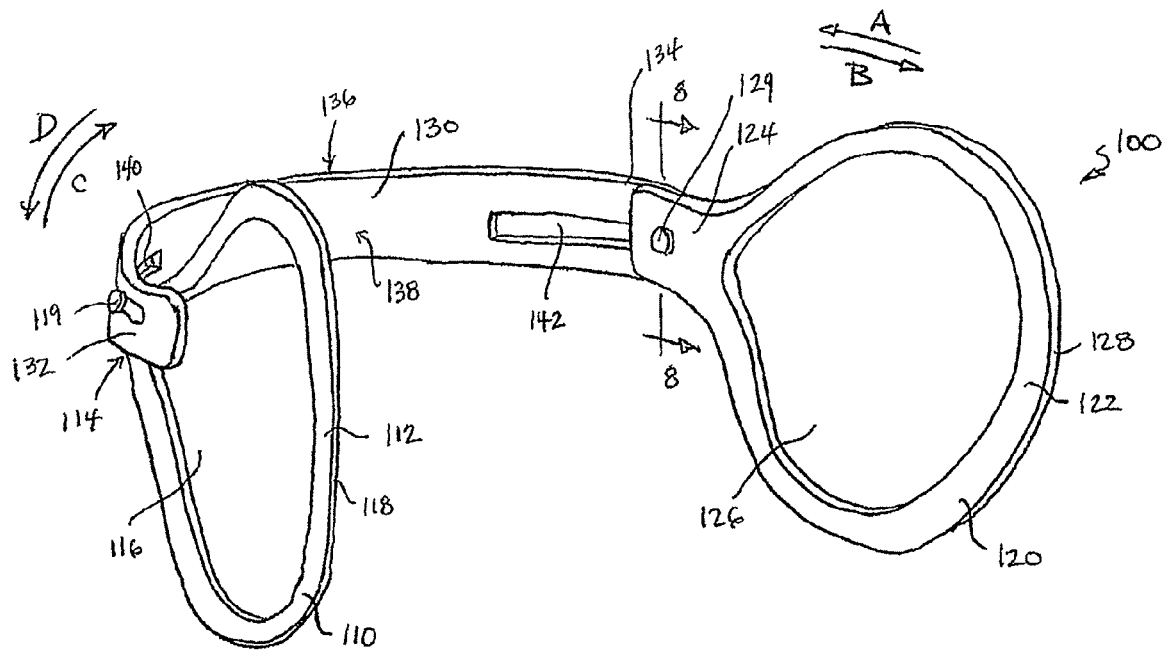
FIG. 7 is a front perspective view of a frame of an ear protection device according to the invention.

An embodiment of a frame for an ear protection device is illustrated in FIGS. 7-13. Referring to FIG. 7, the frame 100 includes ear frame portions 110 and 120 and a band 130. Ear frame portions 110 and 120 are slidably coupled to the band 130.

Ear frame member 110 has a contact region 112 at its distal end 118 and a mounting portion 114 at its opposite end. The contact region 112 is the portion of the ear frame member 110 that applies force to the user's head with the ear protection device 100. The mounting portion 114 of the ear frame member 110 is coupled to the band 130. Ear frame member 110 defines an opening 116.

Similarly, ear frame member 120 has a contact region 122 at its distal end 128 and a mounting portion 124 at its opposite end. The contact region 122 is the portion of the ear frame member 120 that applies force to the user's head with the ear protection device 100. The mounting portion 124 of the ear frame member 120 is coupled to the band 130. Ear frame member 120 defines an opening 126.

In this embodiment, the band 130 includes ends 132 and 134, an outer surface 136 that is disposed away from the user's head, and an inner surface 138 that is disposed proximate to the user's head. The band 130 includes slots 140 and 142 that extend therethrough.

A coupler or connector 119 is inserted through slot 140 on the band 130 to slidably couple the ear frame member 110 to the band 130. In this embodiment, the coupler 119 is a rivet that is inserted through an opening (not shown) in the mounting portion 114 of the ear frame member 110 and the slot 140. In an alternative embodiment, the coupler is a protrusion that is integrally formed with the ear frame member 110 and inserted into the slot 140.

Figure 8:
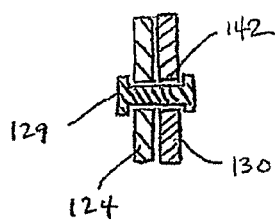
FIG. 8 is a cross-sectional side view of some components of the frame illustrated in FIG. 7 taken along line "8-8."

Similarly, a coupler or connector 129 is inserted through slot 142 on the band 130 to slidably couple the ear frame member 120 to the band 130. Coupler 129 can be similar to coupler 119. Referring to FIG. 8, a coupler 129 is inserted into an opening in the mounting portion 124 of the ear frame member 120 and the slot 142 in the band 130.

In one embodiment, each of the openings in the ear frame members and the coupler can have a substantially square cross-section that maintains the orientation of the ear frame members with respect to the band.

Figure 9:
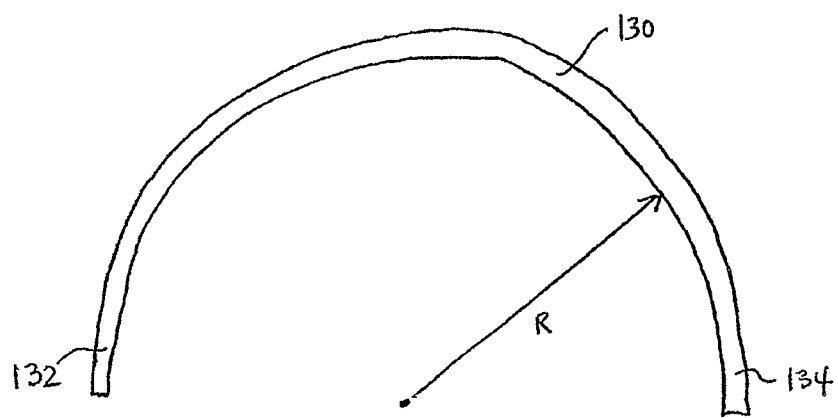
FIG. 9 is a top view of the band of the frame illustrated in FIG. 7.
Figure 10:
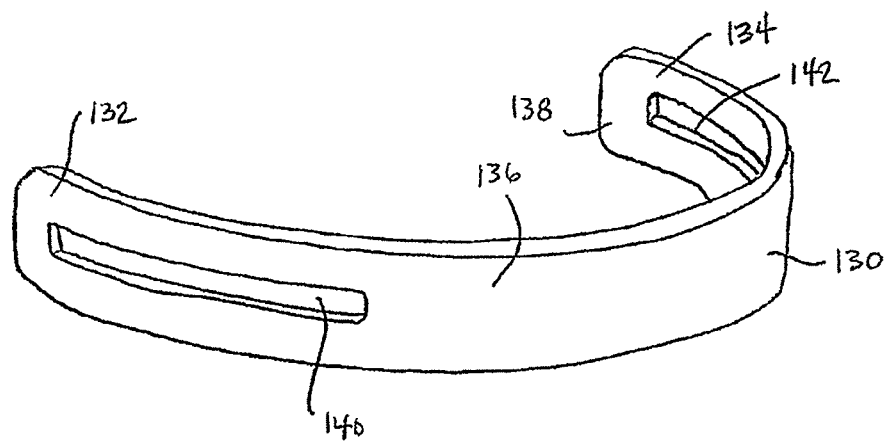
FIG. 10 is a rear perspective view of the band illustrated in FIG. 9.

Referring to FIGS. 9 and 10, the band 130 is illustrated. The band 130 has a constant radius of curvature from end 132 to end 134. The constant radius of curvature facilitates the application of a constant force on the user's head, even though the length of the ear protection device is adjusted.

Figure 11:
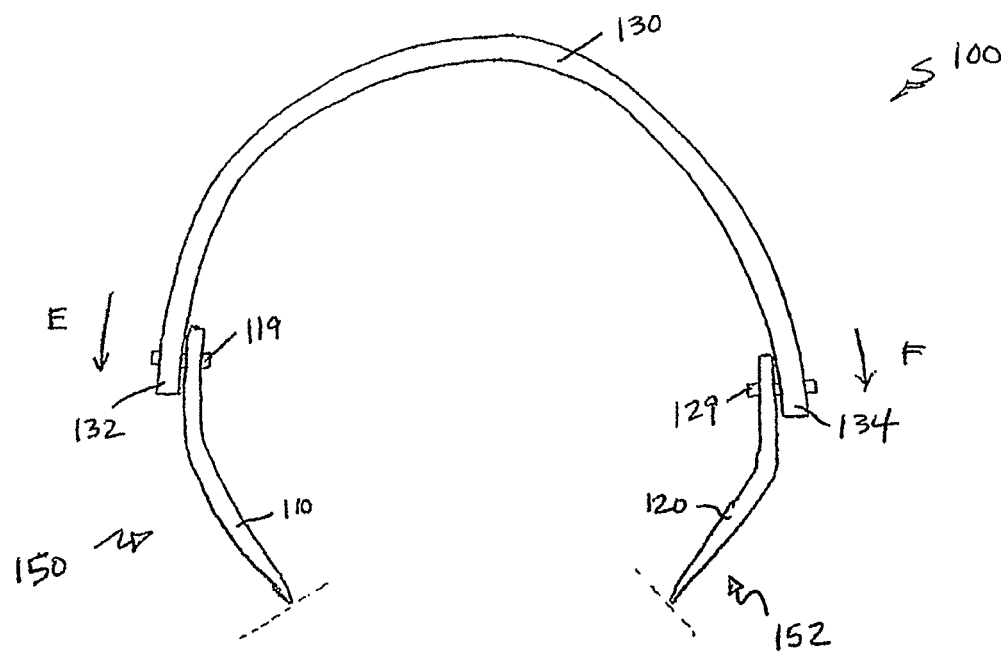
FIG. 11 is a top view of the frame illustrated in FIG. 7 in a first configuration.
Figure 12:
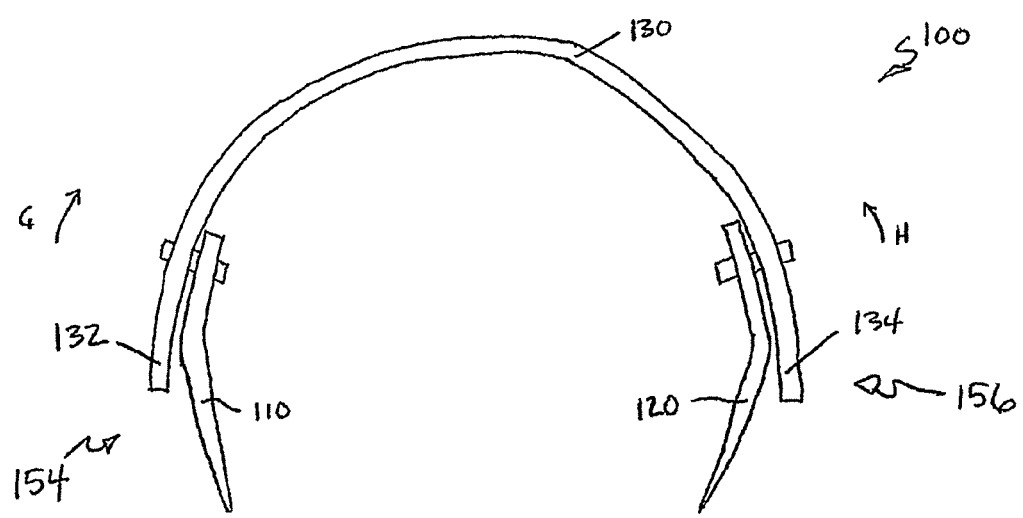
FIG. 12 is a top view of the frame illustrated in FIG. 7 in a second configuration.
Figure 13:
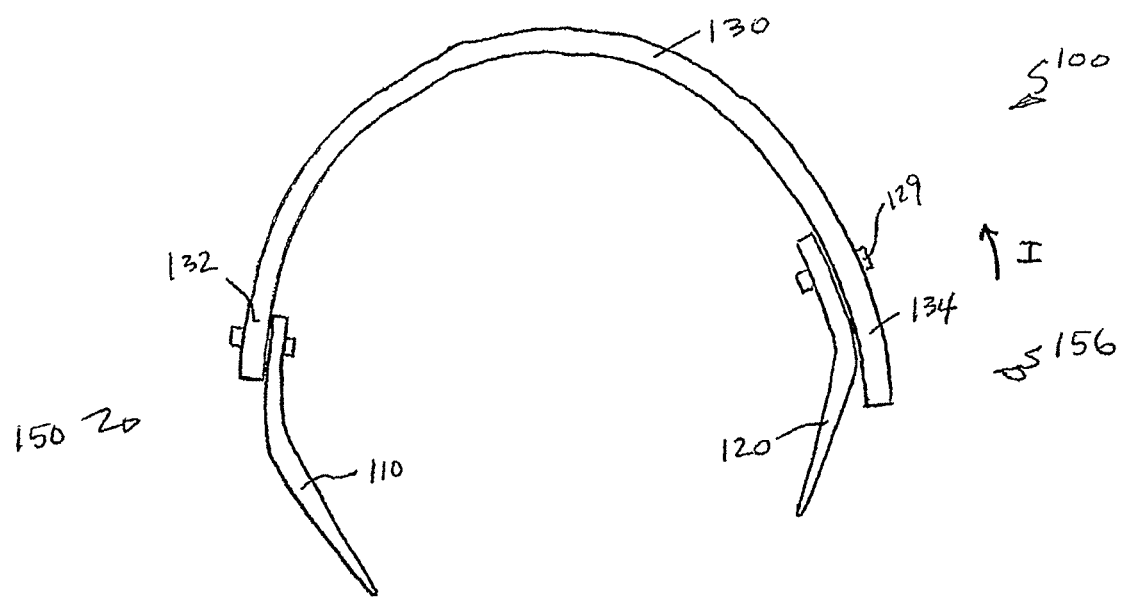
FIG. 13 is a top view of the frame illustrated in FIG. 7 in a third configuration.

Referring to FIGS. 11-13, the ear protection device frame 100 is illustrated in different configurations. The frame 100 includes ear frame member 110, ear frame member 120 and band 130. The ear frame members 110 and 120 can be moved simultaneously and independently relative to the band 130.

In FIG. 11, a fully extended configuration of the ear protection device frame 100 is illustrated. As shown, the ear frame member 110 is moved along the direction of arrow "E" until coupler 119 is moved to the distal end of slot 140 and the ear frame member 110 is in its extended position 150. Similarly, ear frame member 120 is moved along the direction of arrow F until coupler 129 is moved to the distal end of slot 142 and the ear frame member 120 is in its extended position 152.

In the configuration in FIG. 11, the ear frame members 110 and 120 are in their extended positions 150 and 152 and the overall length of the frame 100 is its longest.

In FIG. 12, a fully retracted configuration of the ear protection device frame 100 is illustrated. As shown, the ear frame member 110 is moved along the direction of arrow "G" until coupler 119 is moved to the proximal end of slot 140 and the ear frame member 110 is in its retracted position 154. Similarly, ear frame member 120 is moved along the direction of arrow "H" until coupler 129 is moved to the proximal end of slot 142 and the ear frame member 120 is in its extended position 156. In the configuration illustrated in FIG. 12, the ear frame members 110 and 120 are in their extended positions 154 and 156 and the overall length of the frame 100 is its shortest.

In FIG. 13, an alternative configuration of the ear protection device frame 100 is illustrated. In this configuration, ear frame member 120 is moved along the direction of arrow "I" and the coupler 129 slides along the slot 142 of the band 130. As shown, ear frame member 110 is in its extended position 150 and ear frame member 120 is in its retracted position 156.

Figure 14:
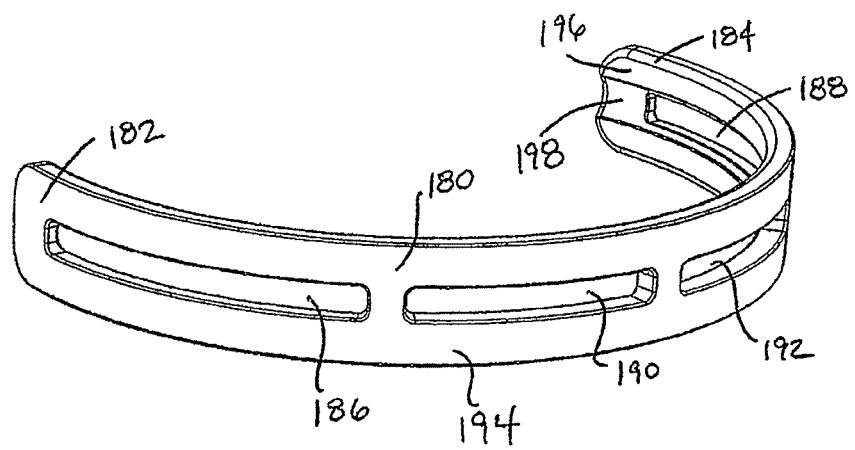
FIG. 14 is a rear perspective view of an alternative embodiment of a band according to the invention.
Figure 15:
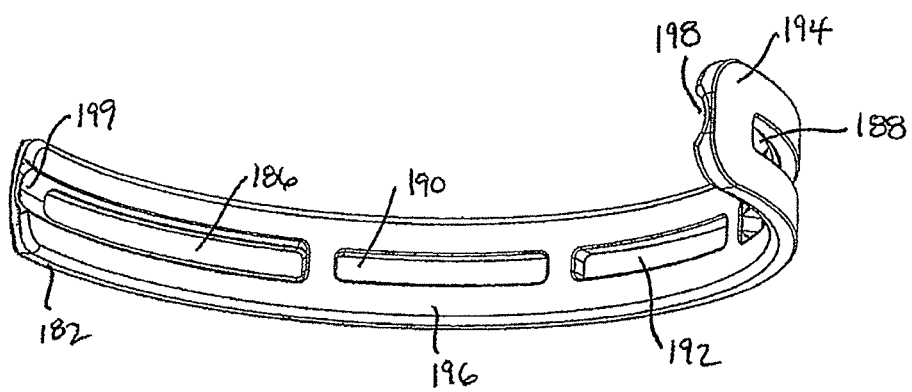
FIG. 15 is a front perspective view of the band illustrated in FIG. 14.

An alternative embodiment of a band for an ear protection device frame is illustrated in FIGS. 14 and 15. In this embodiment, the band 180 has ends 182 and 184 and several slots 186, 188, 190 and 192 that are disposed along the length of the band 180. The length and location of the slots can vary.

Slots 186 and 188 are configured to receive a coupler (not shown in FIGS. 14 and 15) to connect ear frame members to the band 180. The removal of the material from the band 180 to form slots 190 and 192 results in a lower weight of the band 180 and increased flexibility of the band 180. In an alternative embodiment, an ear frame member can be removably coupled to the band 180 via slots 190 and 192.

The band 180 has an outer surface 194 and an opposite inner surface 196. The inner surface 196 includes grooves 198 and 199 formed therein. Each of the grooves 198 and 199 is configured to received an alignment mechanism that is disposed on the ear frame members. In one embodiment, the alignment mechanism is a protrusion molded on an ear piece member.

Figure 16:
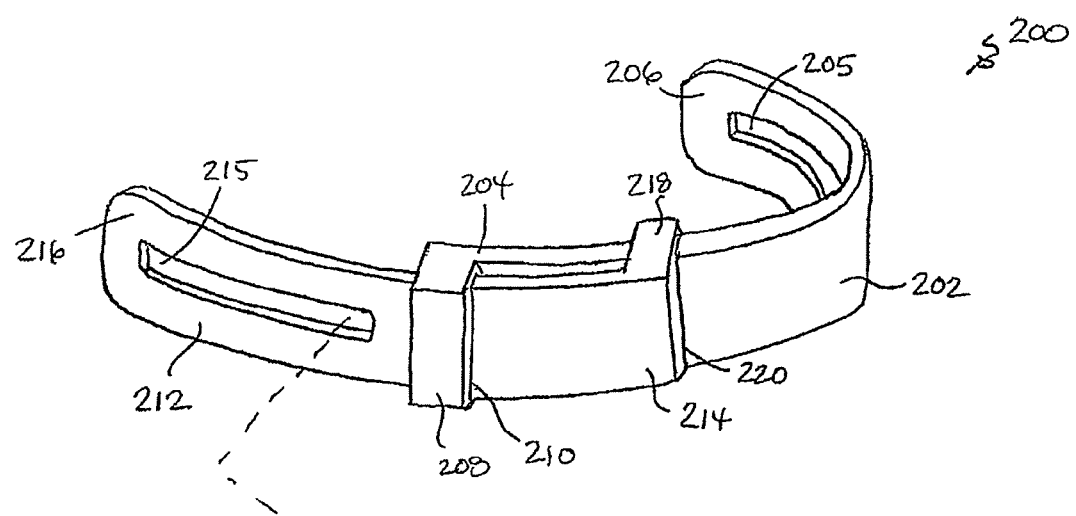
FIG. 16 is a rear perspective view of an alternative embodiment of a band according to the invention.
Figure 16:
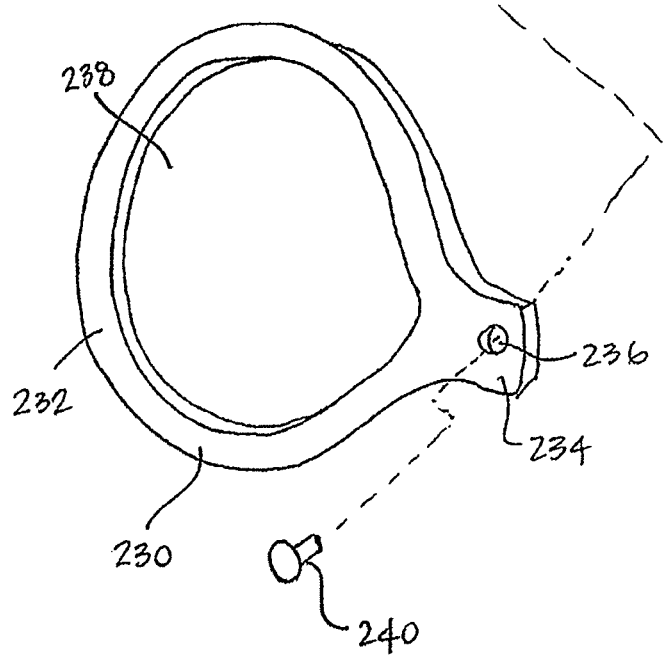

An alternative embodiment of a band for an ear protection device is illustrated in FIG. 16. In this embodiment, the band 200 includes a first band portion 202 and a second band portion 212. The first band portion 202 is movably coupled to the second band portion 212 to allow the length of the band to be adjusted. In this embodiment, the first band portion 202 is slidably coupled to the second band portion 212.

First band portion 202 has ends 204 and 206 and a passageway 208 disposed proximate to end 204. The passageway 208 includes an opening 210 through which a portion of the second band portion 212 can be inserted. Preferably, the opening 210 is configured to be approximately the same size and shape as the cross-section of the second band portion 212. The first band portion 202 has a slot 205 formed therein. In this embodiment, the slot 205 does not extend along the length of the first band portion 202.

Second band portion 212 has ends 214 and 216 and a passageway 218 disposed proximate to end 214. The passageway 218 includes an opening 220 through which a portion of the first band portion 202 can be inserted. Preferably, the opening 220 is configured to be approximately the same size and shape as the cross-section of the first band portion 202. The second band portion 212 also has a slot 215 formed therein. In this embodiment, the slot 215 does not extend along the length of the second band portion 212 and is approximately the same length as the slot 205 in the first band portion 202.

As illustrated in FIG. 16, an ear frame member 230 can be coupled to the second band portion 212. A similarly configured ear frame member can be coupled to the first band portion 202. In various embodiments, the ear frame members can have any configuration or shape.

In this embodiment, ear frame member 230 includes a contact portion 232 that is configured to contact a person's head and a mounting portion 234 that is configured to be coupled to the band 200. In this embodiment, the contact portion 232 includes an opening 238, which can be any size. The mounting portion 234 includes an opening 236 through which a connector 240, such as a rivet or bolt, can be inserted. The connector 240 is subsequently inserted into the slot 215 of the second band portion 212. Similarly, another connector can be inserted through an opening of an ear frame member and into slot 205 of the first band portion 202.

Figure 17:
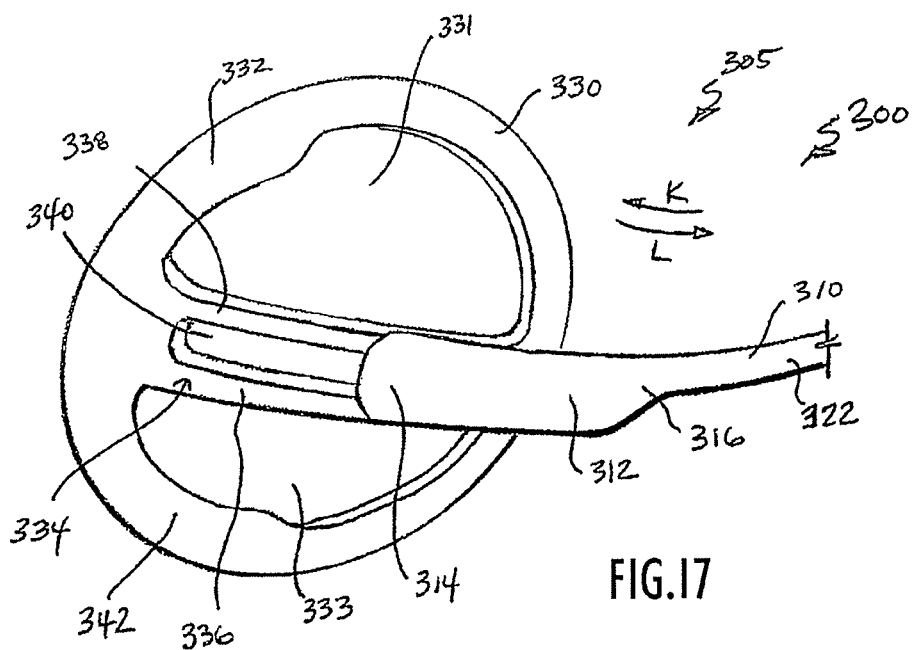
FIG. 17 is a partial outside view of some components of an alternative embodiment of a frame according to the invention.
Figure 18:
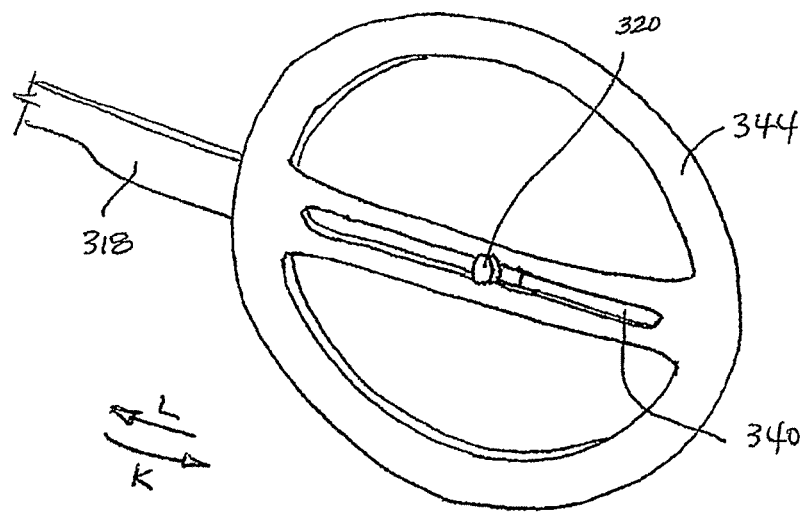
FIG. 18 is a partial inside view of the components of the frame illustrated in FIG. 17.

An alternative embodiment of an ear protection device according to the invention is illustrated in FIGS. 17 and 18. In this embodiment, the ear protection device 300 includes a band 310, a first ear frame member 330 and a second ear frame member (not shown). In FIGS. 17 and 18, only a portion 305 (the band 310 and the first ear frame member 330) of the ear protection device 300 is illustrated. In this implementation, the portion 305 is the side of the ear protection device 300 that contacts a user's left ear. The remaining portion of the ear protection device 300 (the other portion of band 310 and the second ear frame member) is a mirror image of portion 305 which is illustrated.

Band 310 of ear protection device 300 has a curved configuration along its length and includes a first end 314 and a coupling portion 312 proximate to the first end 314. The band 310 includes a second end (not shown) that is opposite to the first end 314. In this embodiment, the band 310 has a main body portion 322 that has a different thickness than the coupling portion 312. The additional thickness of the coupling portion 312 provides greater stability and strength to the band 310.

The band 310 also includes an outer surface 316 and an opposite inner surface 318. A protrusion 320 is coupled to the inner surface 318 of the band 310. In one embodiment, the protrusion 320 is integrally molded with the band 310. In another embodiment, the protrusion is formed separately from the band and coupled thereto using any conventional method or technique.

In this embodiment, the ear frame member 330 includes a contact portion 332 and a coupling portion 334. The contact portion 332 is a substantially circular shaped ring. The coupling portion 334 extends from one side of the contact portion 332 to an opposite side of the contact portion 332. Contact portion 332 is integrally formed with the coupling portion 334. In an alternative embodiment, the contact portion can be formed separately from the coupling portion and coupled thereto using any conventional method or technique. The coupling portion 334 forms two openings 331 and 333 through the ear frame member 330. The relative sizes of the two openings 331 and 333 can vary. The ear frame member 330 includes an inner surface 344 and an opposite outer surface 342.

The coupling portion 334 includes a slot 340 that is formed by supports 336 and 338. The ear frame member 330 is coupled to the band 310 by inserting the coupler 320 through the slot 340 of the ear frame member 330. The ear frame member 330 can be moved relative to the band 310 along the directions of arrows "K" and "L." The length of the slot 340 determines the range of movement of the ear frame member 330 relative to the band 310.

Figure 19:
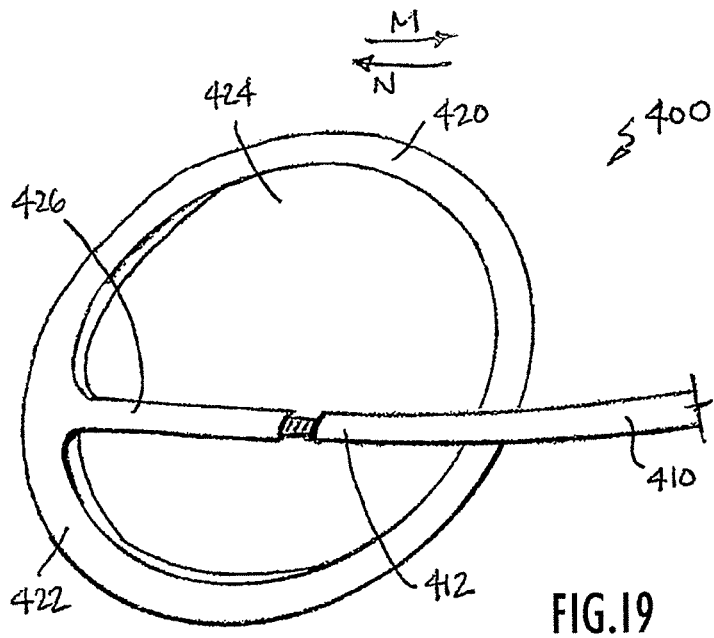
FIG. 19 is a partial outside view of some components of an alternative embodiment of a frame according to the invention.
Figure 20:
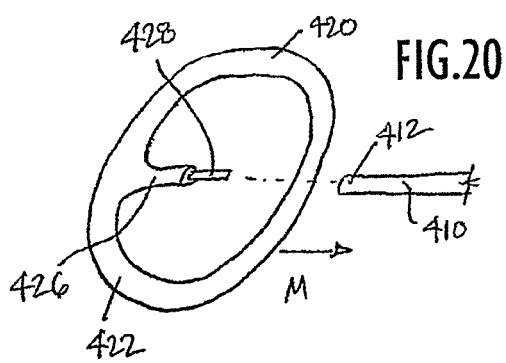
FIG. 20 is an exploded partial outside view of the components of the frame illustrated in FIG. 19.
Figure 21:
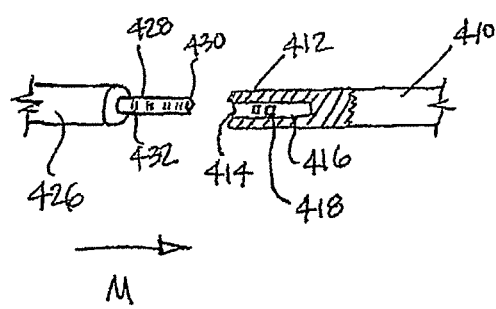
FIG. 21 is partial cross-section of the components illustrated in FIG. 20.

An alternative embodiment of an ear protection device is illustrated in FIGS. 19-21. In this embodiment, the ear protection device 400 includes a band 410, a first ear frame member 420 and a second ear frame member (not shown). Similar to the previous embodiment, only a portion of ear protection device 400 is illustrated and described. First ear frame member 420 is illustrated as coupled proximate to one end of the band 410, and a second ear frame member is coupled proximate to the opposite end of the band 410.

Band 410 has an end 412 with an opening 414 and a recess or channel 416 (see FIG. 21). In FIG. 21, a partial cross-sectional view of end 412 is illustrated. Within channel 416 are several projections or ridges 418 formed on a surface defining the channel 416. The function of the projections is discussed in greater detail below.

In this embodiment, the ear frame member 420 includes a body 422 that defines an opening 424. While the body 422 is illustrated as being substantially ring shaped, in alternative embodiments, the body of the ear frame member can have any shape or configuration. The ear frame member 420 includes a coupling portion 426 that is formed with the body 422. In this embodiment, the coupling portion 426 is coupled at one end to one side of the body 422 and extends rearwardly toward the other side of the body 422. While the coupling portion 426 is illustrated as being integrally formed with the body 422, in an alternative embodiment, the coupling portion 426 and the body can be formed separately and coupled together.

The coupling portion 426 includes an extension 428 that protrudes from an end of the coupling portion 426. In this embodiment, the extension 428 is narrower than the coupling portion 426. The end of the coupling portion 426 that surrounds the extension 428 forms an abutment surface. As illustrated in FIG. 21, the extension 428 includes an end 430 and several recesses 432 along its length. The recesses 432 are configured to receive the projections 418 within the channel 416 when the extension 428 is inserted into the channel 416.

Referring to FIG. 19, the ear frame member 420 is moved along the direction of arrow "M" to couple the ear frame member 420 to the band 410. Similarly, the ear frame member 420 is moved along the direction of arrow "N" to separate the ear frame member 420 from the band 410. When the ear frame member 420 is moved along the direction of arrow "M" as shown in FIGS. 20 and 21, the extension 428 of the coupling member 426 is inserted into the channel 416 of the band 410. The projections 418 are configured to engage the recesses 432 of the extension 428, and such engagement provides resistance to movement and allows the ear frame member 420 to be mounted at several positions with respect to the band 410. For example, the ear frame member 420 can be mounted with the abutment surface of the coupling portion 426 spaced apart from the end of the band 410 (see FIG. 19) or the ear frame member 420 can be mounted with the abutment surface of the coupling portion 426 proximate to the end surface of the band 410. The ability to mount the ear frame member 420 at multiple locations relative to the band 410 allows the overall length of the ear protection device frame, as measured from a distal end of a first ear frame member to a distal end of a second ear frame member, to be adjusted.

In an alternative embodiment, the projections can be located on the extension of the coupling portion 426 and the recesses can be formed in the channel of the band 410. The projections and recesses would cooperate in the same manner in which the projections 418 and recesses 432 operate as described above.

Figure 22:
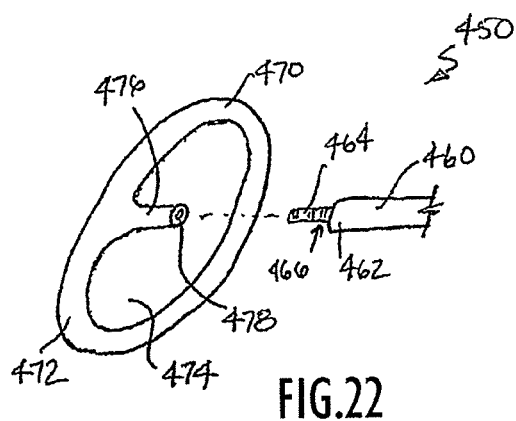
FIG. 22 is an exploded partial outside view of the components of an alternative embodiment of a frame according to the invention.

An alternative embodiment of an ear protection device is illustrated in FIG. 22. This embodiment is substantially similar to the ear protection device embodiment illustrated in FIGS. 19-21, with the differences described below.

In this embodiment, the ear protection device 450 includes a band 460 and an ear frame member 470. The band 460 includes an end 462 and an extension 464. The extension 464 includes a series of recesses 466.

The ear frame member 470 includes a body 472 defining an opening 474 and a coupling portion 476. An end of the coupling portion 476 includes an opening 478 into which the extension 464 of the band 460 can be inserted. The ear frame member 470 can be coupled to the band 460 at one of several positions, similar to ear frame member 420 as described above.

An alternative embodiment of an ear protection device is illustrated in FIG. 23. In this embodiment, the ear protection device has a frame 500 that includes a band 510, a first ear frame member 530 and a second ear frame member (not shown). The structure of the second ear frame member is a mirror-image of the structure of the first ear frame member 530. Moreover, the coupling of the second ear frame member to the band 510 is the same as the coupling of the first ear frame member 530 to the band 510.

In this embodiment, the band 510 includes band portions 512 and 514 that are coupled together at end portion 516. The band portions 512 and 514 and end portion 516 collectively form a slot 515. The formation of the slot 515 increases the flexibility of the band 510 and reduces the overall weight of the band 510.

Band 510 includes an extension 518 that protrudes from the end portion 516. Extension 518 has a substantially rectangular cross-sectional shape. In alternative embodiments, the extension of the band can have a cross-sectional shape other than rectangular, such as circular, a square, etc. Extension 518 is integrally formed with the end portion 516 of the band 510. In alternative embodiments, the extension 518 may be separately formed and subsequently coupled to the end portion 516 of the band 510. Extension 518 includes a surface 520 in which several recesses 522 are formed. The function of the recesses 522 will be described in detail below.

Ear frame member 530 includes a body 532 that defines an opening 534 and a mounting portion 536 coupled to the body 532. The mounting portion 536 includes an end 538 and an opening 540. The mounting portion 536 includes an internal channel in communication with the opening 540. Several projections are located on an inner surface of the internal channel.

The opening 540 is configured to receive the extension 518 of the band 510 when the ear frame member 530 is moved toward the band 510 along the direction of arrow "O." The recesses 522 are configured to receive one or more of the projections in the internal channel of the mounting portion 536. In an alternative embodiment, the projections can be disposed on the extension of the band and the recesses can be located on a surface in the internal channel of the mounting portion.

The ear frame member 530 can be moved relative to the band 510 along the directions of the arrows "O" and "P." The ear frame member 530 can be disposed at several positions along the extension 518 of the band 510.

An alternative embodiment of a frame for an ear protection device is illustrated in FIGS. 24 and 25. In this embodiment, the frame 600 includes a band 610 and an ear frame member 620 coupled proximate to one end of the band 610. Another ear frame member (not shown) is coupled proximate to the opposite end of the band 610.

The band 610 has a main portion 611 and an end portion 612 with a coupling portion 614. The coupling portion 614 has a width dimension "w" that is larger than the width of the main portion 611 of the band 610. The coupling portion 614 includes an opening 616 formed therein.

Ear frame member 620 includes a body 620 that defines an opening 624. The body 620 includes a coupling portion 626 that enables the ear frame member 620 to be coupled to the band 610. The coupling portion 626 is formed by the two ends or wrap portions 628 and 630 of the body 620. Each of the ends has a curved configuration. Collectively, the wrap portions 628 and 630 form an opening 632 through which the band 610 can be inserted (see FIG. 25). The configuration of the opening 632 is such that it frictionally receives the band 610.

In this embodiment, the ear frame member 620 can be made of a resilient material, such as metal. To couple the ear frame member 620 and the band 610, the coupling portion 614 of the band 610 is inserted into the opening 632 of the ear frame member 620.

Figure 26:
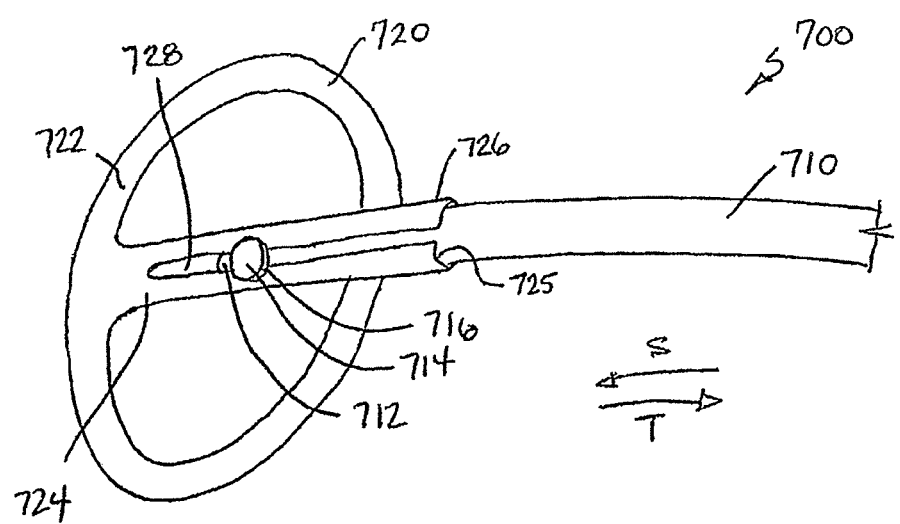
FIG. 26 is a partial outside view of some components of an alternative embodiment of a frame according to the invention.

An alternative embodiment of a frame for an ear protection device is illustrated in FIG. 26. In this embodiment, the frame 700 includes a band 710 and an ear frame member 720. The band 710 has an end 712 and an opposite end (not shown). A coupler 714 is connected to the band 710. The coupler 714 includes a coupling portion or head 716, the function of which is described in detail below.

Ear frame member 720 includes a body 722 and a coupling portion 724. The coupling portion 724 has a distal end 725 and forms a sleeve 726. The coupling portion 724 has a slot 728 that extends from the distal end 725 along most of the length of the sleeve 726.

To couple the band 710 and the ear frame member 720, the band 710 is moved along the direction of arrow "S" and end 712 is inserted into the sleeve 726. At the same time, coupler 714 engages slot 728. The friction between the coupler 714 and the edges of slot 728 and the surfaces of the band 710 and the inner surfaces of the sleeve 726 retains the ear frame member 720 on the band 710.

To remove the band 710 and the ear frame member 720 from each other, the band 710 is moved along the direction of arrow "T" and end 712 is removed from the sleeve 726. The other ear frame member is selectively coupleable to the band 710 in a similar manner.

An alternative embodiment of a frame for an ear protection device is illustrated in FIGS. 27-30. In this embodiment, the frame 800 includes a band 810, a first ear frame member 830 and a second ear frame member (not shown). The ear frame members are coupled to opposite ends of the band 810.

Figure 27:
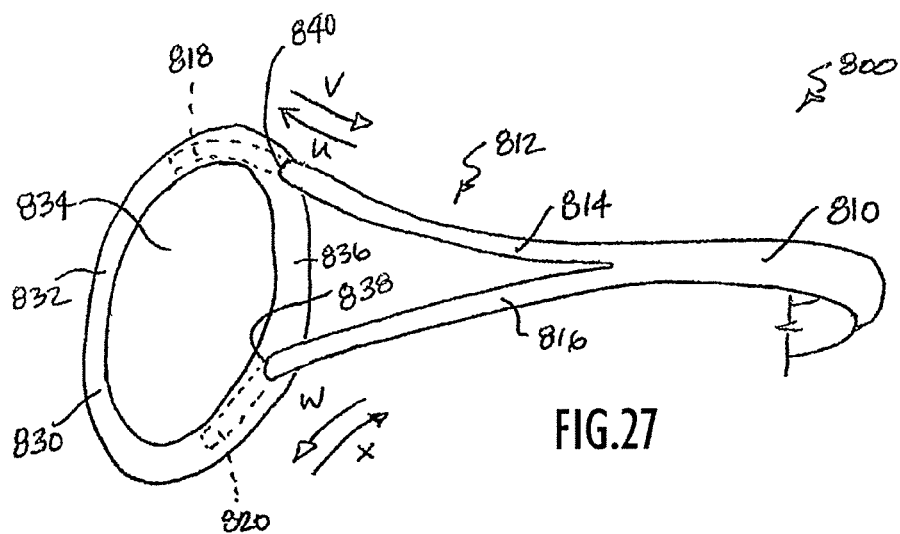
FIG. 27 is a partial outside view of some components of an alternative embodiment of a frame according to the invention.
Figure 29:
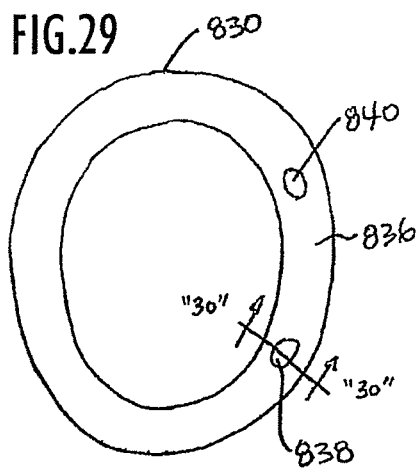
FIG. 29 is a side view of the band of the frame illustrated in FIG. 27.
Figure 28:
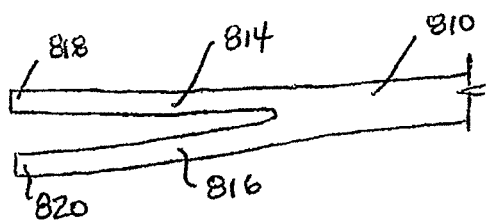
FIG. 28 is a side view of an ear frame member of the frame illustrated in FIG. 27.

As illustrated in FIGS. 27-28, band 810 includes an end portion 812 that is formed by two band portions 814 and 816. Band portions 814 and 816 have ends 818 and 820, respectively. Preferably, the band 810 is made of a semi-rigid material that has flexible characteristics, such as plastic.

Ear frame member 830 includes a body 832 that defines an opening 834. The body 832 is substantially frusto-conically shaped (see FIG. 30). The body 832 includes an outer surface 836 with spaced apart openings 838 and 840 through the body 832. Opposite the outer surface 836 is an inner surface 842.

Referring to FIG. 27, to couple the band 810 and the ear frame member 830, band portion 814 is moved along the direction of arrow "U" and is inserted into opening 840 in the body 832. Band portion 816 is moved along the direction of arrow "W" and is inserted into opening 838 in the body 832. The band portions 814 and 816 are frictionally retained in the openings 840 and 838, respectively. The band portions 814 and 816 are inserted so that ends 818 and 820 extend along the inner surface 842 of the body 832. The overall length of the frame can be adjusted by moving the ear frame member 830 along the band portions 814 and 816. To remove the ear frame member 830 from the band 810, the band portions 814 and 816 are moved along the directions of arrows "V" and "X," respectively.

Figure 31:
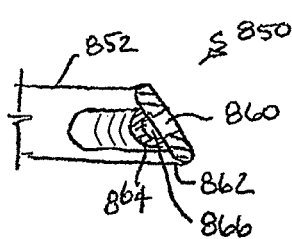
FIG. 31 is a cross-sectional view of an alternative embodiment of an ear frame member according to the invention.
Figure 30:
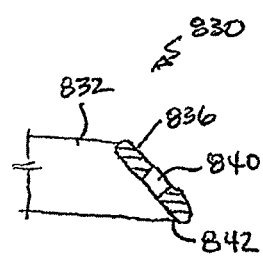
FIG. 30 is a cross-sectional view of the ear frame member illustrated in FIG. 29 taken along the line "30-30."

An alternative embodiment of an ear frame member is illustrated in FIG. 31. In this embodiment, the ear frame member 850 has a generally frusto-conical configuration and can be used with a band similar to band 810 described above. Ear frame member 850 includes a body 852 with an outer surface 856 and at least one opening 860 therethrough.

The body 852 includes an inner surface 862 to which a guide 864 is coupled. The guide 864 and the inner surface 862 form a channel 866 into which one of the band portions 814 and 816 can be inserted after passing through opening 860. The guide 864 extends along only a portion of the inner surface 862. The length of the guide 864 and the channel 866 determines the extent to which one of the band portions can be inserted. For example, band portion 816 can be inserted into opening 860 and moved until end 820 engages the distal internal surface of the channel 866. The ear frame member 850 includes another opening (not shown) and similar guide and channel structure along a portion of the inner surface 862.

Figure 32:
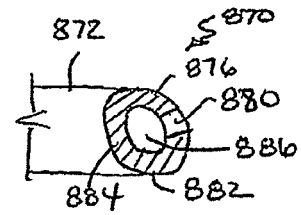
FIG. 32 is a cross-sectional view of an alternative embodiment of an ear frame member according to the invention.

An alternative embodiment of an ear frame member is illustrated in FIG. 32. In this embodiment, the ear frame member 870 has a generally toroidal configuration and can be used with a band similar to band 810 described above. Ear frame member 870 includes a body 872 with an outer surface 876 and an opening 880. The body 872 has an inner or contact surface 882. The body 872 has a generally circular cross-sectional shape and defines a channel 886 into which one of the band portions 814 and 816 can be inserted after passing through opening 880. In this embodiment, channel 886 extends along the length of the body 872. In a different embodiment, channel 886 extends only a portion of the length of the body 872. In another embodiment, there is another opening on the body of the ear frame member and a separate channel is associated with that opening. The structures of the ear frame members 850 and 870 increase the control over the ends of the band portions after the ends are inserted into the ear frame members 850 and 870.

Figure 33:
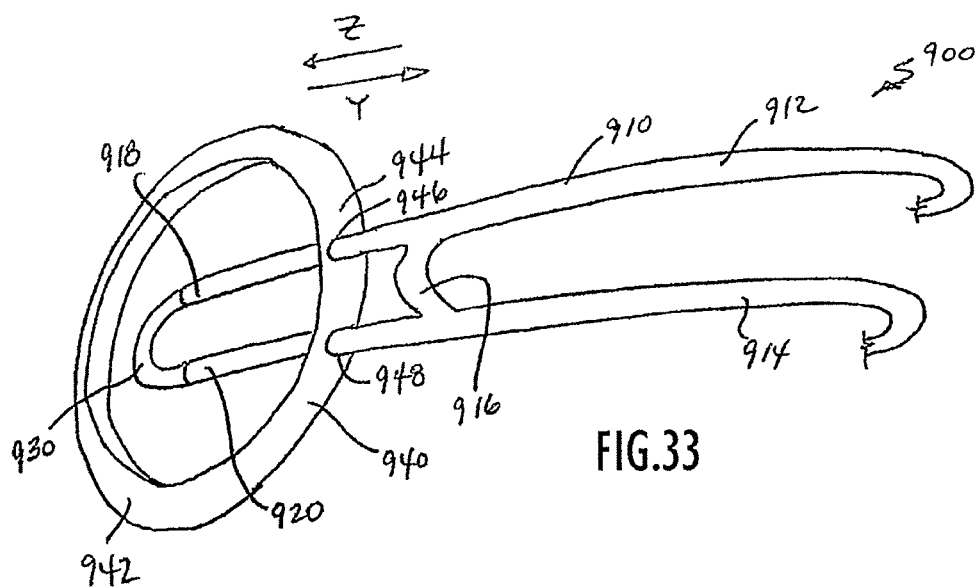
FIG. 33 is a perspective view of some components of an alternative embodiment of a frame according to the invention.
Figures 34, 35:
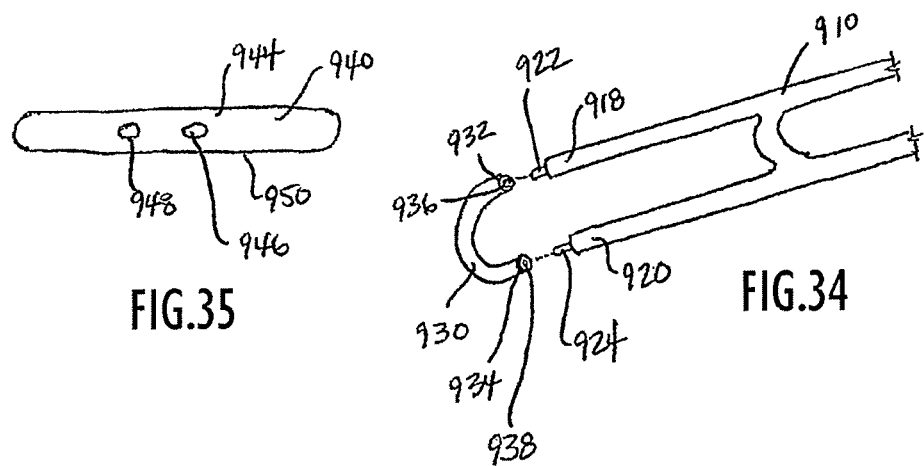
FIG. 34 is an exploded perspective view of some components of the band of the frame illustrated in FIG. 33.
FIG. 35 is an end view of the ear frame member of the frame illustrated in FIG. 33.

An alternative embodiment of a frame for an ear protection device is illustrated in FIGS. 33-35. In this embodiment, the frame 900 has a band 910, a first ear frame member 940 and a second ear frame member (now shown). The second ear frame member has a similar structure to that of the first ear frame member.

Ear frame member 940 includes a body 942 with an outer surface 944 with openings 946 and 948 formed therein. The body 942 includes an inner or contact surface 950.

The band 910 includes band portions 912 and 914 and a support portion 916 disposed therebetween. The support portion 916 couples the band portions 912 and 914 together and provides structural stability. As illustrated in FIG. 34, band portion 912 has an end 918 and an extension 922 extending therefrom. Similarly, band portion 914 has an end 920 and an extension 924 extending therefrom.

The band 910 includes a coupler 930 that is removably coupled to the ends 918 and 920 of the band 910. The coupler 930 is substantially U-shaped and includes ends 932 and 934 with openings 936 and 938, respectively. Opening 936 is configured to receive extension 922 of band end 918 and opening 938 is configured to receive extension 924 of band end 920. The openings 936 and 938 and the channels in communication with them are configured to slidably receive the extensions 922 and 924 and couple the coupler 930 to the band ends 918 and 920 via friction.

However, before coupler 930 is coupled to band portions 912 and 914, the band portions 912 and 914 are inserted into the ear frame member 940 through openings 946 and 948, respectively, along the direction of arrow "Z." Once the band portions 912 and 914 have been inserted, the coupler 930 is coupled to band ends 918 and 920 as previously described. The ear frame member 940 is then slidably mounted on the band 910 and adjustable to change the overall length of the frame 900.

To remove the ear frame member 940, the coupler 930 is disconnected from the band ends 918 and 920 and the band portions 912 and 914 are removed from the openings 946 and 948, respectively. The other ear frame member is coupled to the band 910 in the same manner.

An alternative embodiment of a frame for an ear protection device is illustrated in FIGS. 36-39. In this embodiment, the frame 1000 has a band 1010, a first ear frame member 1030 coupled to the band 1010, and a second ear frame member (not shown) coupled to the band 1010. The first ear frame member 1030 includes a piece of fabric 1050, such as fleece, coupled thereto along the inner side of the ear frame member 1030. The fabric 1050 provides comfort to the user when the ear protection device is worn. The second ear frame member includes a similar piece of fabric. The pieces of fabric can be removably or fixedly coupled to the ear frame members.

Figure 38:
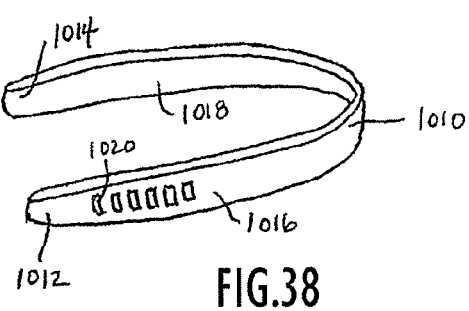
FIG. 38 is a perspective view of the band of the frame illustrated in FIG. 36.

As illustrated in FIG. 38, the band 1010 includes ends 1012 and 1014, an outer surface 1016 and an inner surface 1018. Several recesses 1020 are formed in the outer surface 1016 of the band 1010 proximate to end 1012 and to end 1014.

Figure 37:
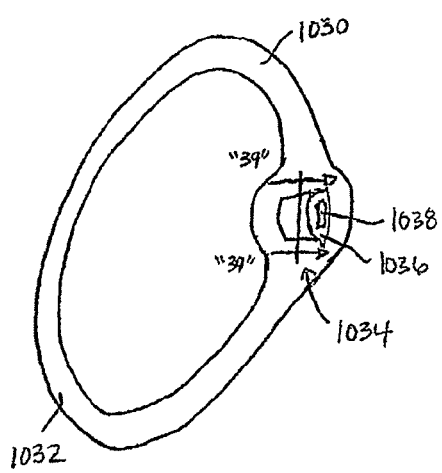
FIG. 37 is a perspective view of an ear frame member of the frame illustrated in FIG. 36.
Figure 39:
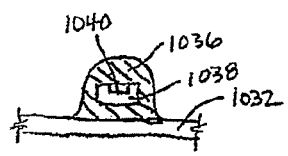
FIG. 39 is a partial cross-sectional view of the ear frame member illustrated in FIG. 37 taken along line "39-39."

Referring to FIG. 37, ear frame member 1030 includes a body 1032 with a coupling portion 1034. The coupling portion 1034 is configured to couple the ear frame member 1030 to the band 1010. The coupling portion 1034 includes a mount 1036 that has a channel 1038. As illustrated in FIG. 39, a projection 1040 extends inwardly in the channel 1038.

Figure 36:
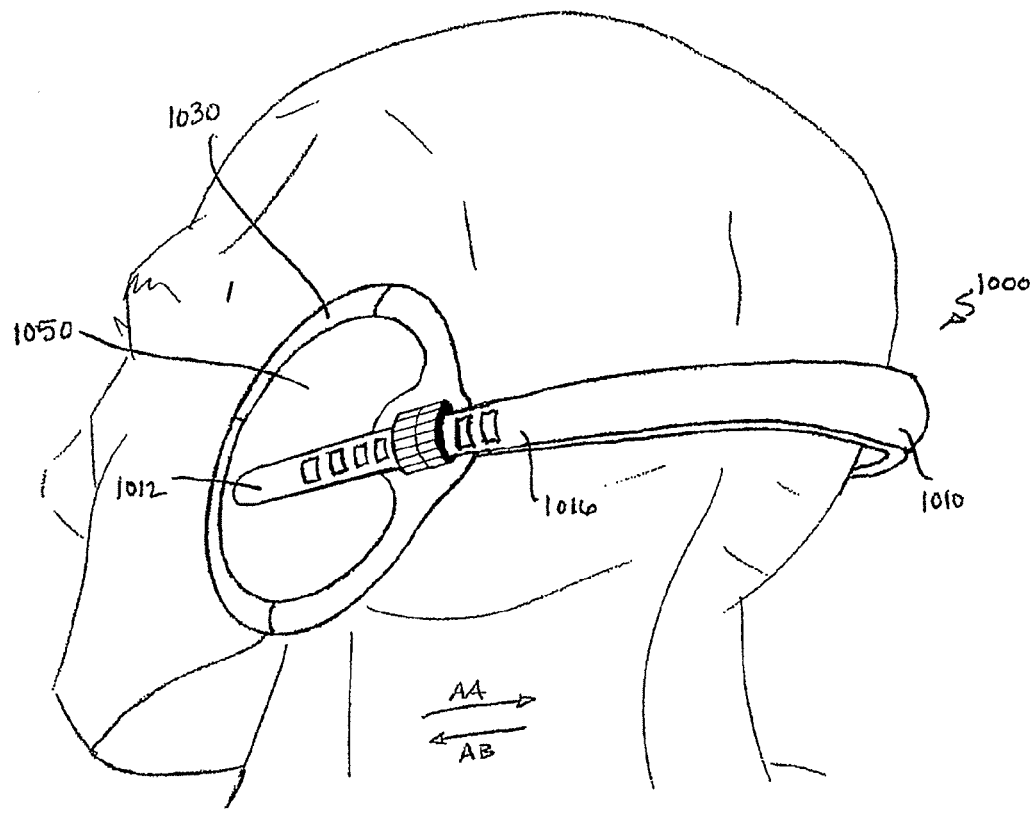
FIG. 36 is a perspective view of some components of an alternative embodiment of a frame according to the invention.

To couple the ear frame member 1030 and the band 1010, end 1012 of the band 1010 is inserted into the channel 1038 in the mount 1036 along the direction of arrow "AB" in FIG. 36. As the end 1012 passes through the channel 1038, the projection 1040 engages the recesses 1020 on the band 1010 and retains the band 101 and the ear frame member 1030 together. To separate the ear frame member 1030 and the band 1010, the band is moved along the direction of arrow "AA" until it is disconnected from the mount 1036.

The multiple recesses 1020 provide different positions along the band 1010 in which the ear frame member 1030 can be disposed. The multiple positions allow the overall length of the band 1010 to be adjusted. The ear frame member coupled to the opposite end of the band 1010 from ear frame member 1030 is configured and operates in a similar manner.

Figure 40:
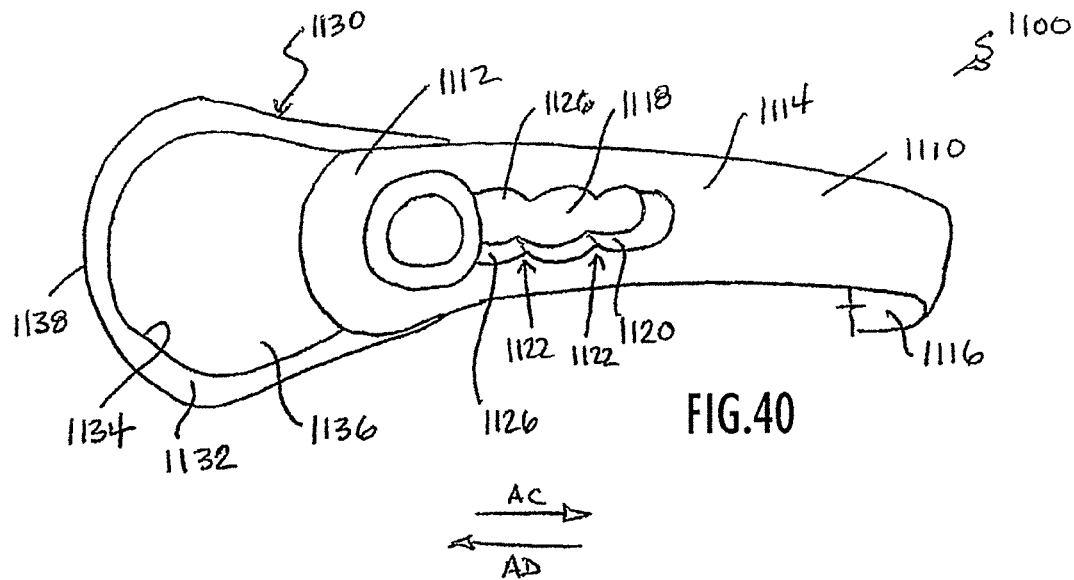
FIG. 40 is a side view of some components of an alternative embodiment of a frame according to the invention.
Figure 41:
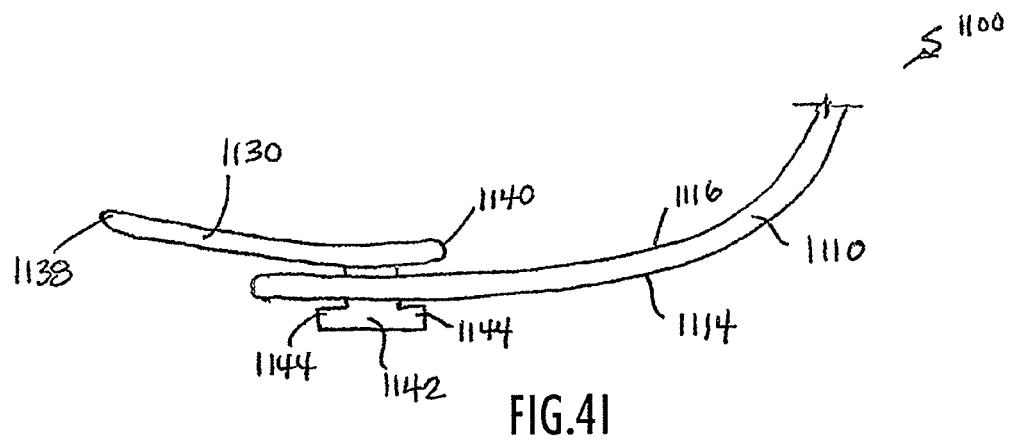
FIG. 41 is a top view of the components of the frame illustrated in FIG. 40.
Figure 42:
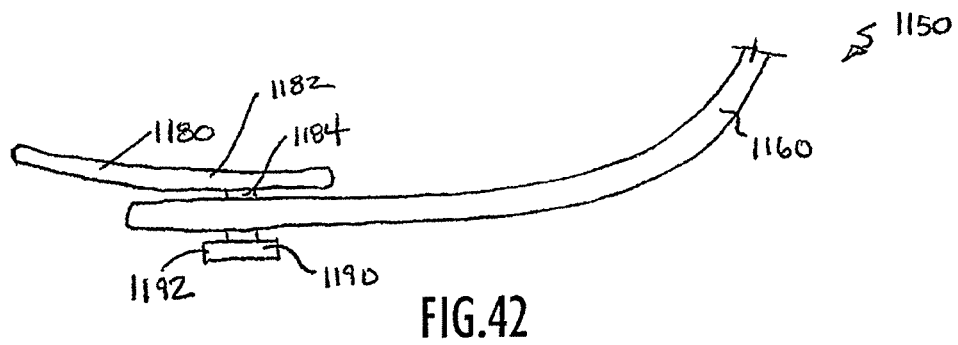
FIG. 42 is a top view of some components of an alternative embodiment of a frame according to the invention.

An alternative embodiment of a frame for an ear warmer is illustrated in FIGS. 40-42. In this embodiment, the frame 1100 has a band 1110, a first ear frame member 1130 coupleable to the band 1110, and a second ear frame member (not shown) coupleable to the band 1110.

The band 1110 has opposite ends (only end 1112 is shown), and outer surface 1114, and an inner surface 1116. Proximate to end 1112, a slot 1118 is formed which extends from the outer surface 1114 to the inner surface 1116. The slot 1118 is formed by a surface 1120 that includes a series of ridges 1122, 1124 and recesses 1126, 1128. In different embodiments, the quantity of ridges and recesses along the surface of slot 1120 can vary.

The ear frame member 1130 includes a body 1132 with an edge 1134 and an opening 1135 that can be covered by a fabric material 1136 on one side. The body 1132 includes a distal end 1138 and a proximal end 1140. The proximal end 1140 is coupled to the band 1110 by coupler 1142, which is connected to the body 1132. The coupler 1142 is configured to be slidably received in the slot 1118. The coupler 1142 and the ear frame member 1130 can be moved back and forth along the directions of arrows "AC" and "AD" as shown in FIG. 40. The ridges 1122 and recesses 1126 form different stops or positions for the coupler 1142 in slot 1118.

In FIG. 41, the coupler 1142 includes an integrally formed flange 1144 which retains the ear frame member 1130 and the band 1110 together. To couple the ear frame member 1130 and the band 1110, the coupler 1142 is inserted or snapped into the slot 1118 and the flange 1144 retains the two structures together.

In an alternative embodiment, shown in FIG. 42, the frame 1150 has a band 1160 and an ear frame member 1180 that is substantially the same as ear frame member 1130. In this embodiment, the ear frame member 1180 has a body 1182 to which a post 1184 is coupled. Post 1184 can be integrally formed with the body 1182. A flange portion 1192 is formed when a threaded member 1190, such as a cap, is threaded onto an end of the post 1184. In alternative embodiments, the flange portion 1192 can be coupled to the post 1184 using other techniques.

An alternative embodiment of a frame for an ear warmer is illustrated in FIGS. 43-47. In this embodiment, the frame 1200 has a band portion 1210, a first ear frame member 1230 and a second ear frame member (not shown).

Band portion 1210 includes band 1212 and 1214, which are configured to extend around a user's head. Band 1212 has two ends, one of which, end 1216 is illustrated. Band 1214 has two ends, one of which, end 1218 is illustrated. Ends 1216 and 1218 are biased toward each other by biasing member 1215. A similar biasing member is disposed proximate to the opposite ends of the bands 1212 and 1214.

The frame 1200 includes fabric 1260 which forms a shell for a portion of the frame 1200. Fabric 1260 includes two channels 1262 and 1264 that extend along the length of the fabric 1260. Channel 1262 is formed by a seam 1266 and channel 1264 is formed by a seam 1268. Band 1212 is longer than the length of the fabric 1260 and extends out of each end of the channel 1262. Similarly, band 1214 is longer than the length of the fabric 1260 and extends out of each end of the channel 1264.

Figure 43:
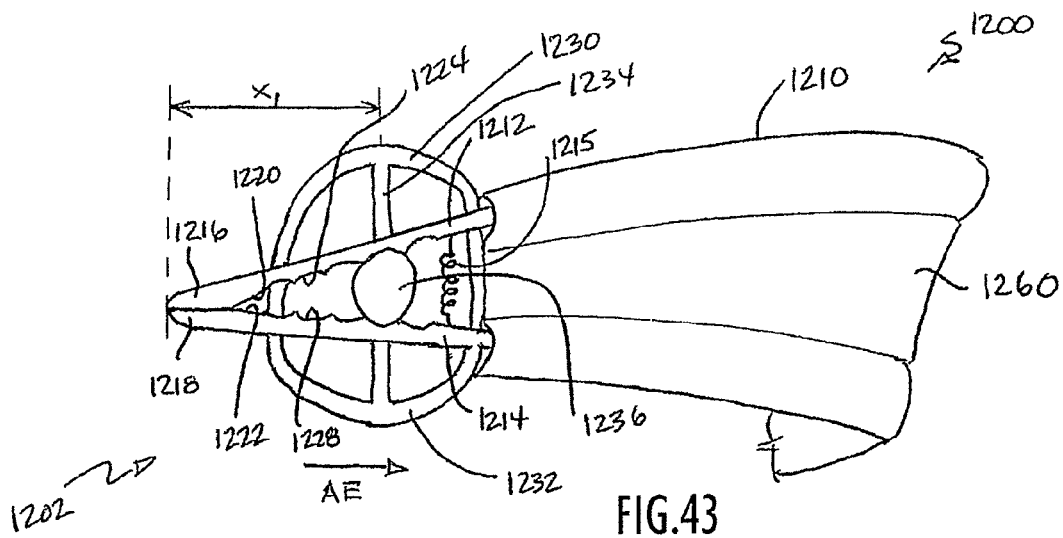
FIG. 43 is a side view of some components of an alternative embodiment of a frame in a first configuration.
Figure 44:
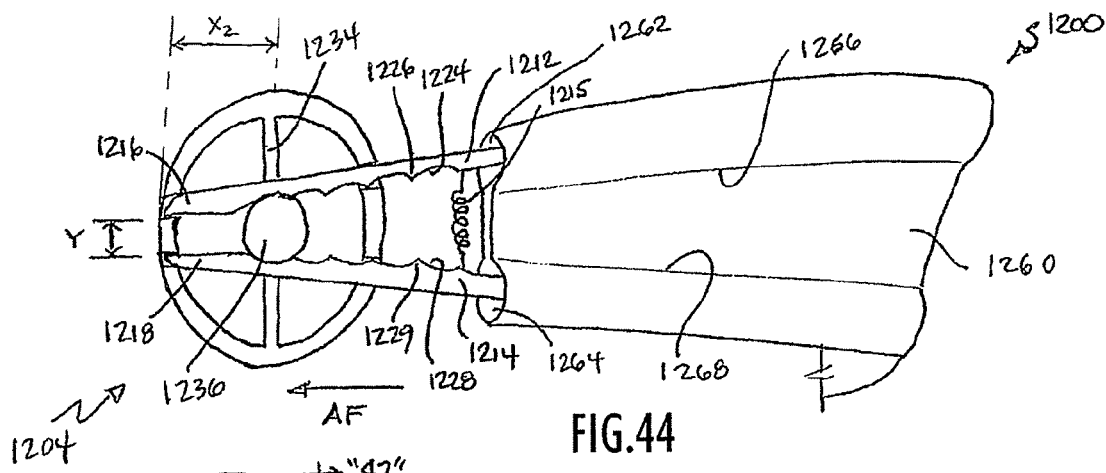
FIG. 44 is a side view of the components illustrated in FIG. 43 in a second configuration.

As illustrated in FIGS. 43 and 44, band 1212 has a contact surface 1220 that includes alternating recesses 1224 and ridges 1226. Similarly, band 1214 has a contact surface 1222 that includes alternating recesses 1228 and ridges 1229. The function of the recesses 1224 and 1228 and the ridges 1226 and 1229 is described below.

Figure 45:
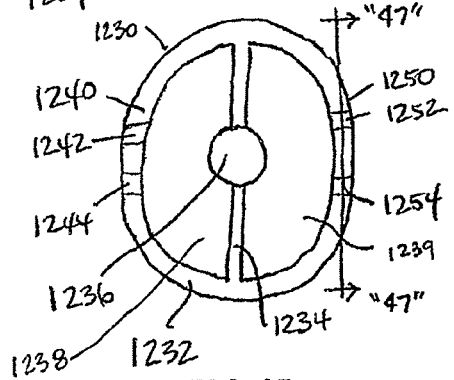
FIG. 45 is a side view of an ear frame member of the frame illustrated in FIG. 43.
Figure 46:
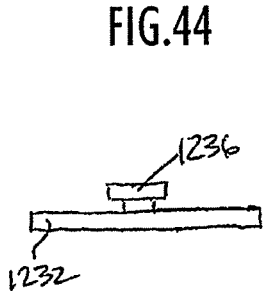
FIG. 46 is an end view of the ear frame member illustrated in FIG. 45.
Figure 47:
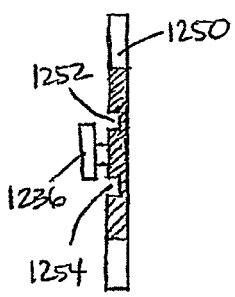
FIG. 47 is a cross-sectional side view of the ear frame member illustrated in FIG. 45 taken along line "47-47."

Referring to FIGS. 45-47, the ear frame member 1230 is illustrated. Ear frame member 1230 includes a body 1232 that is substantially circular and a support 1234 that extends across the body 1232. The body 1232 and the support 1234 form openings 1238 and 1239 on the sides of the support 1234. A coupler 1236 is connected to the support 1234. Preferably, the coupler 1236 has a post and an enlarged head.

The body 1232 of the ear frame member 1230 includes a first side 1240 and a second side 1250. Along the first side 1240, grooves or slots 1242 and 1244 are formed. Similarly, along the second side 1250, grooves or slots 1252 and 1254 are formed. The depth and configuration of the grooves or slots 1252 and 1254 are illustrated in FIG. 47.

To couple the ear frame member 1230 to the band 1210, the ends 1216 and 1218 of the band portions 1212 and 1214 are separated and inserted through the respective slots on the body 1232. For example, band portion 1212 is inserted through slots 1242 and 1252. Similarly, band portion 1214 is inserted through slots 1244 and 1254. The coupler 1236 on the ear frame member 1230 is captured between surface 1220 of band portion 1212 and surface 1222 of band portion 1214. The coupler 1236 can be positioned within any of the recesses 1224 and 1228 of the band portions 1212 and 1214.

As the coupler 1236 and ear frame member 1230 are moved along the direction of arrow "AE" in FIG. 43, the center of the coupler 1236 can be located a distance X1 from the distal tips of ends 1216 and 1218. In this configuration, the ends 1216 and 1218 of the band portions 1212 and 1214 are in contact with each other.

To lengthen the frame 1200, the ear frame member 1230 and coupler 1236 are moved along the direction of arrow "AF" in FIG. 44. As coupler 1236 is moved along arrow "AF," the ends 1216 and 1218 are moved apart from each other a distance Y and the center of the coupler 1236 is located a distance X2 from the distal tips of ends 1216 and 1218. In this example, the distance X2 is less than the distance X1.

In this embodiment, the ear frame members are independently movable along the band portions 1212 and 1214 of the frame 1200. Preferably, the coupler of each ear frame member is located the same distance from the ends of the band portions of the frame. In other embodiments, the distances from the ends of the band portions to the couplers of the ear frame members can vary.

Figure 48:
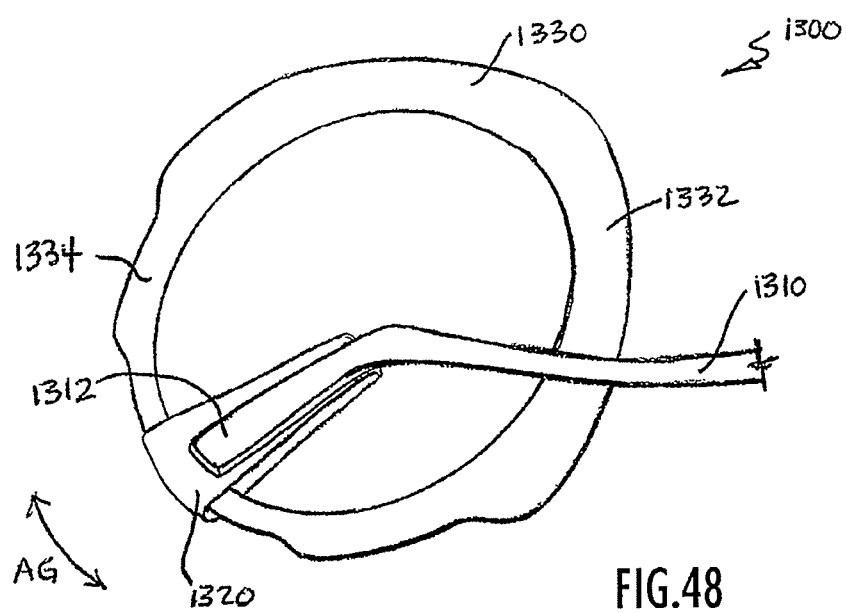
FIG. 48 is a side view of some components of an alternative embodiment of a frame according to the invention.
Figure 49:
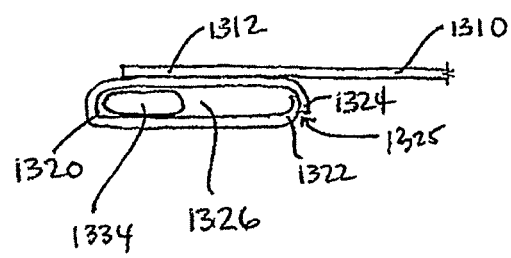
FIG. 49 is a top view of some components of the band of the frame illustrated in FIG. 48.

An alternative embodiment of a frame for an ear protection device is illustrated in FIGS. 48 and 49. In this embodiment, the frame 1300 includes a band 1310, which can be a one piece band or a multiple piece band, and two ear frame members, one of which, ear frame member 1330, is shown. The ear frame members are coupled to opposite ends of the band 1310 in a similar manner.

As shown, band 1310 has an end 1312 to which a coupler 1320 is connected. The coupler 1320 can be made of plastic, metal or similar material and has ends 1322 and 1324 that are coupleable together at connection point 1325. The coupler 1320 is configured to form an opening 1326 through which a portion of the ear frame member 1330 can be inserted.

The ear frame member 1330 includes a first portion 1332 having a first thickness and a second portion 1334 having a second thickness which is different than the first thickness. The ear frame member 1330 can be rotated along the direction of arrow "AG" as shown in FIG. 48 to change the portion of the ear frame member that contacts part of the user's head.

As illustrated in FIG. 49, portion 1334 of the ear frame member 1330 is located within the coupler 1320. To couple the ear frame member 1330 and the band 1310, ends 1322 and 1324 of the coupler 1320 are separated and a portion of the ear frame member 1330 is inserted therebetween. The ends 1322 and 1324 are connected together by any conventional mechanism, such as a snap arrangement, a groove and pin arrangement, etc. Alternatively, the material of the coupler 1320 may retain its configuration after repeated uses and therefore returns to its configuration illustrated in FIG. 49. In another embodiment, the end 1324 of the coupler 1320 can be extended longer than it is shown in FIG. 49 and thereby hooking around a portion of the end 1322 to couple the ends 1322 and 1324 together.

Once the ends 1322 and 1324 of the coupler 1320 are connected together, the ear frame member 1330 can be adjusted along arrow "AG" as desired. To separate the ear frame member 1330 and the band 1310, the ends 1322 and 1324 are separated and ear frame member 1330 can be removed from the coupler 1320.

Figure 50:
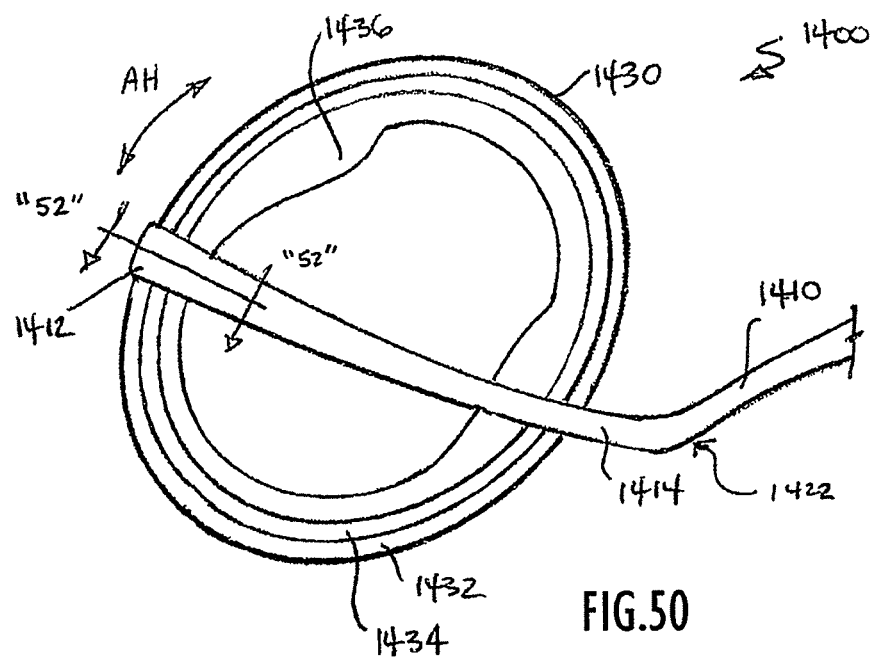
FIG. 50 is a side view of some components of an alternative embodiment of a frame according to the invention.
Figure 51:
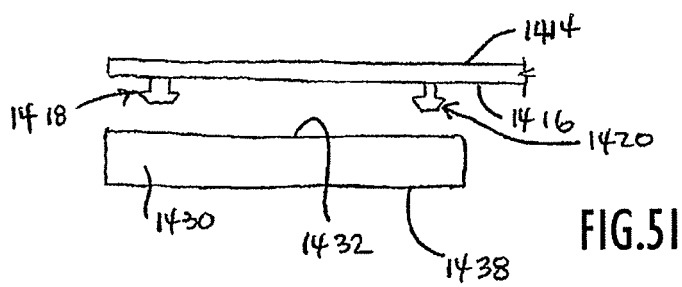
FIG. 51 is an exploded top view of some components of the frame illustrated in FIG. 50.
Figure 52:
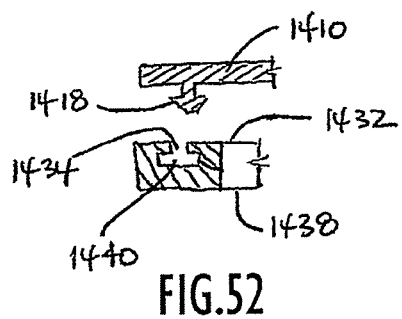
FIG. 52 is a cross-sectional top view of some components of the frame illustrated in FIG. 50, taken along line "52-52" in an exploded relationship.

An alternative embodiment of a frame for an ear protection device is illustrated in FIGS. 50-52. In this embodiment, the frame 1400 includes a band 1410 and two ear frame members coupled proximate to opposite ends of the band 1410 (only ear frame member 1430 is illustrated). Ear frame member 1430 is disposed on the inside of the band 1410. The band 1410 is coupled to the ear frame member 1430 at locations on opposite sides of the ear frame member 1430.

Band 1410 includes an end 1412, an outer surface 1414 that faces away from the user when the ear protection device is worn, and an opposite inner surface 1416. Band 1410 is illustrated as having a bend 1422, but in different embodiments, the band 1410 does not necessarily have the bend 1422. Coupled to inner surface 1416 are projections 1418 and 1420, each of which in this embodiment has an enlarged head portion.

Ear frame member 1430 includes an outer surface 1432 and an inner surface 1438. Ear frame member 1430 has a substantially circular configuration. A slot 1434 is formed in the outer surface 1432 of the ear frame member 1430 and is in communication with a groove 1440. The width of the slot 1434 is narrower than the width of the groove 1440. As shown in FIG. 52, the projection 1418 is insertable into the slot 1434. The enlarged head portion of the projection 1418 passes through the slot 1434 and is disposed within the groove 1440. At that point, the narrower portion of the projection 1418 is disposed within the slot 1434. Projection 1420 is similarly coupled to the ear frame member 1430. In other words, the ear frame member 1430 is press fit or snapped onto the band 1410 by inserting the projections 1418 and 1420 into the slot 1434.

When the ear frame member 1430 is coupled to the band 1410, the projections 1418 and 1420 are movably disposed in slot 1434 and groove 1440 and the ear frame member 1430 can be rotated along the directions of arrow "AH" as shown in FIG. 50. To remove the ear frame member 1430, a user pulls on the ear frame member 1430 with sufficient force to disengage the projections 1418 and 1420 on the band 1410 from the slot 1434 on the ear frame member 1430.

An alternative embodiment of a frame for an ear protection device is illustrated in FIGS. 53-56. In this embodiment, the frame 1500 includes a band 1510 with an ear frame member coupled to each end of the band 1510. As done with previously described embodiments, only one of the ear frame members is described for reasons of simplicity only.

Referring to FIGS. 53 and 54, the band 1510 has an end 1512 with a coupling portion 1514. The coupling portion 1514 is a curved piece of material with a distal tip 1515. The coupling portion 1514 is configured so that the distal tip 1515 does not contact the band 1510, thereby forming a passage 1516. As a result, the coupling portion 1514 defines a receptacle 1518 in communication with the passage 1516.

Ear frame member 1520 is substantially circular in shape. In this embodiment, the ear frame member 1520 has a body 1522 that defines an opening 1524. The body 1522 of the ear frame member 1520 has portions with different or varying thicknesses. Referring to FIG. 55, a thin portion 1526 of the body 1522 and a thick portion 1528 of the body 1522 are illustrated. As shown in FIG. 56, the body 1522 includes an upper or outer surface 1530 and an inner or contact surface 1532 which contacts the user's head when the ear protection device is being worn.

To couple the ear frame member 1520 to the band 1510, a portion of the ear frame member 1520 is inserted into the passage 1516 and snapped into place within the receptacle 1518. The coupling portion 1514 is configured to couple the ear frame member 1520 to the band 1510. A user may rotate the ear frame member 1520 relative to the end 1512 of the band 1510 along the directions of arrow "AI." The frictional forces between the surfaces of the ear frame member 1520 and the coupling portion 1514 retain the ear frame member 1520 in a particular position or orientation with respect to the end 1512 of the band 1510.

The variation in thickness of the ear frame member 1520 also assists with the repositioning and holding of the ear frame member 1520 in an orientation. As the ear frame member 1520 is rotated and the width of the ear frame member 1520 passing through the coupling portion 1514 increases, the frictional forces between the surfaces of the ear frame member 1520 and the coupling portion 1514 increase. At the same time, the coupling portion 1514 must expand to accommodate the increased cross-sectional dimension of the ear frame member 1520. As a thicker portion of the ear frame member 1520 passes through the coupling portion 1514, the resistance to movement of the ear frame member 1520 relative to the band 1510 increases.

As illustrated in FIG. 56, the cross-sectional shape of the ear frame member 1520 is frusto-conical. In an alternative embodiment illustrated in FIG. 57, the ear frame member 1540 includes an outer surface 1550 and an inner or contact surface 1552. The inside surface 1556 and the outside surface 1554 are generally curved and can be shaped so as to match the configuration of the receptacle 1518 in the end 1512 of the band 1510. In other embodiments, the ear frame member 1540 can have different cross-sectional shapes.

Figure 58:
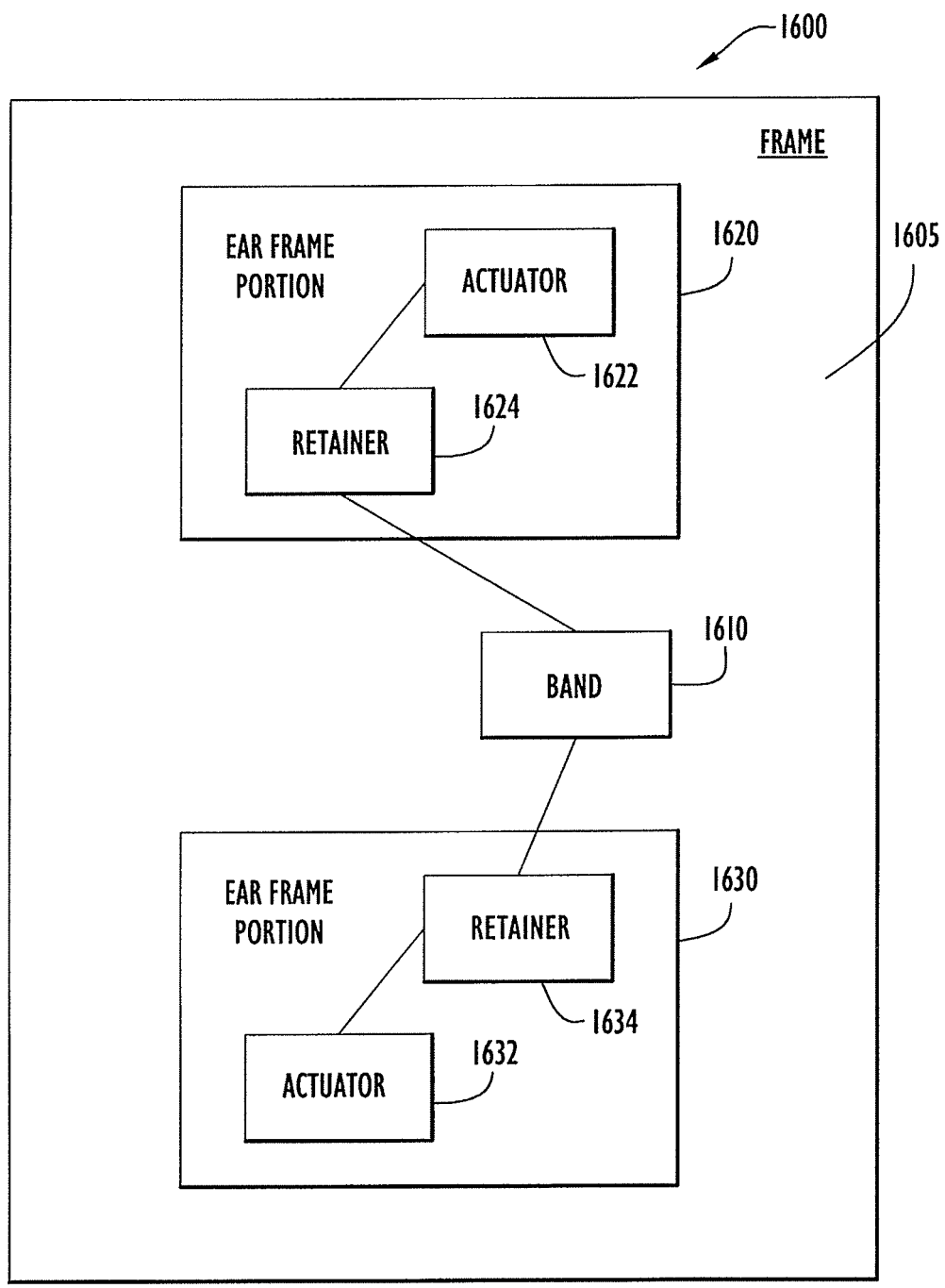
FIG. 58 is a block diagram of an embodiment of an ear protection device according to the invention.

A block diagram of an alternative embodiment of an ear protection device is illustrated in FIG. 58. In this embodiment, the ear protection device 1600 includes a frame 1605. Frame 1605 is configured to extend around the band of a user's head. Frame 1605 includes a band 1610 and ear frame members or portions 1620 and 1630.

In one embodiment, band 1610 can be a single piece band that is not adjustable in length. In other embodiments, band 1610 can include multiple pieces that can be moved relative to each other to adjust the length of the band 1610.

Ear frame portion 1620 is coupled to the band 1610. Preferably, the ear frame portion 1620 is movably coupled the band 1610 to allow adjustment of the ear frame portion 1620 relative to the band 1610. The ear frame portion 1620 includes an actuator 1622 and a retainer 1624. The retainer 1624 is configured to couple the ear frame portion 1620 and the band 1610 together. The actuator 1622 is configured to cause movement of the retainer 1624 between a retaining position and a non-retaining position.

Similarly, ear frame portion 1630 is coupled to the band 1610. Preferably, the ear frame portion 1630 is movably coupled to the band 1610 to allow for adjustment. The ear frame portion 1630 includes an actuator 1632 and a retainer 1634. The retainer 1634 is configured to couple the ear frame portion 1630 to the band 1610. The actuator 1632 is configured to cause movement of the retainer 1634 between a retaining position and a non-retaining position.

Figure 59:
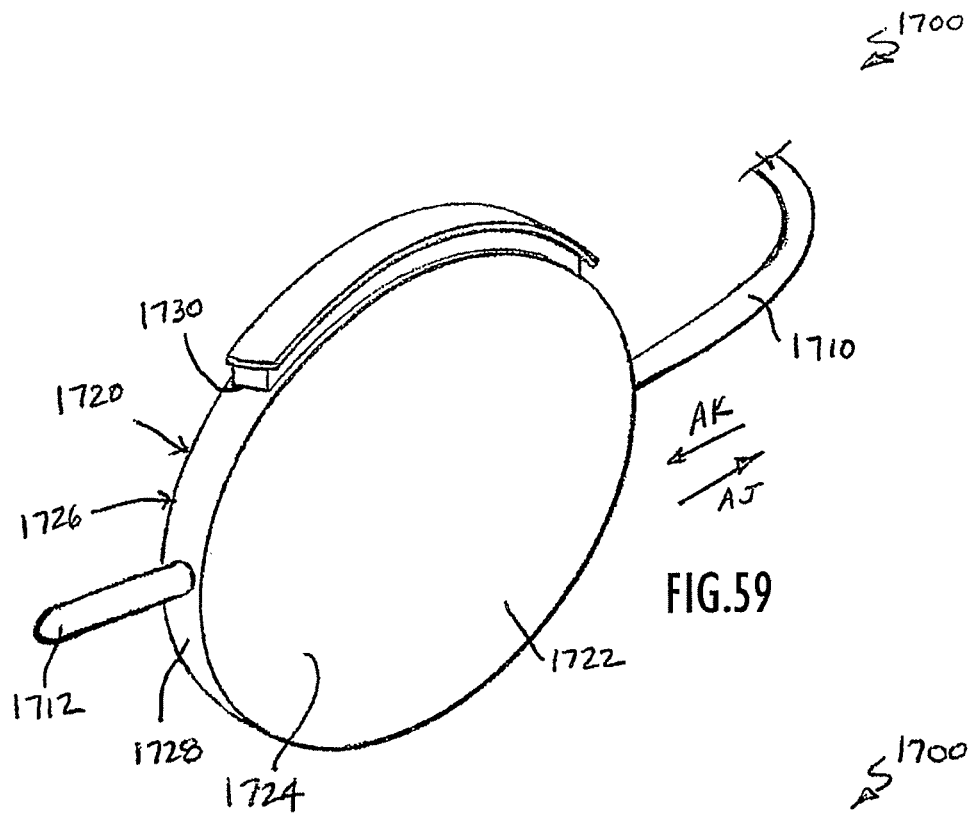
FIG. 59 is a side perspective view of some components of an alternative embodiment of an ear protection device according to the invention.
Figure 60:
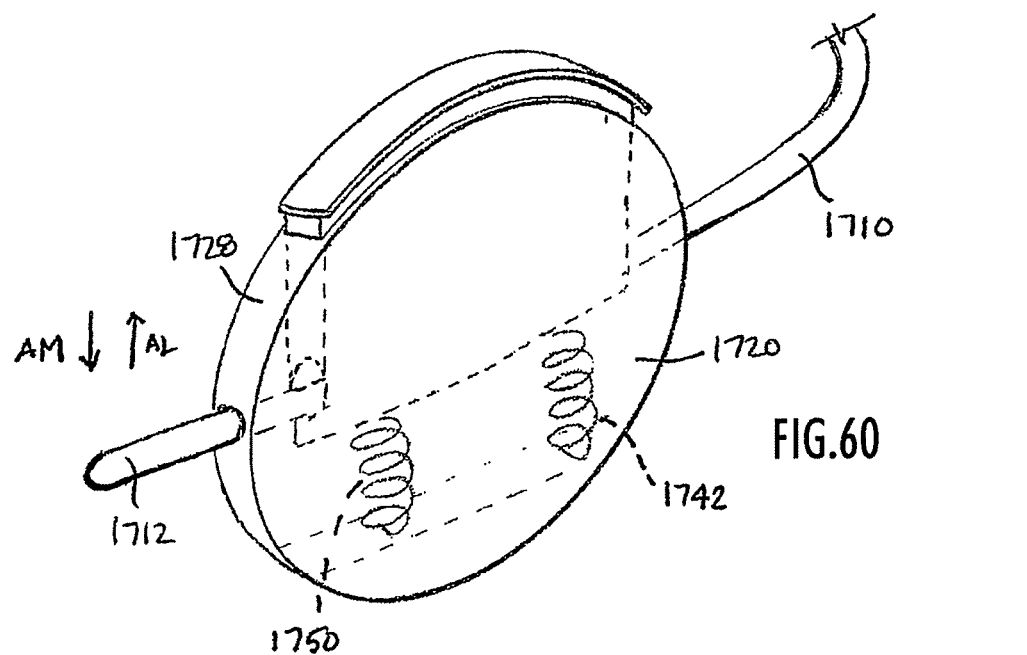
FIG. 60 is a side perspective view of the ear protection device illustrated in FIG. 59 showing some of the internal components.
Figure 61:
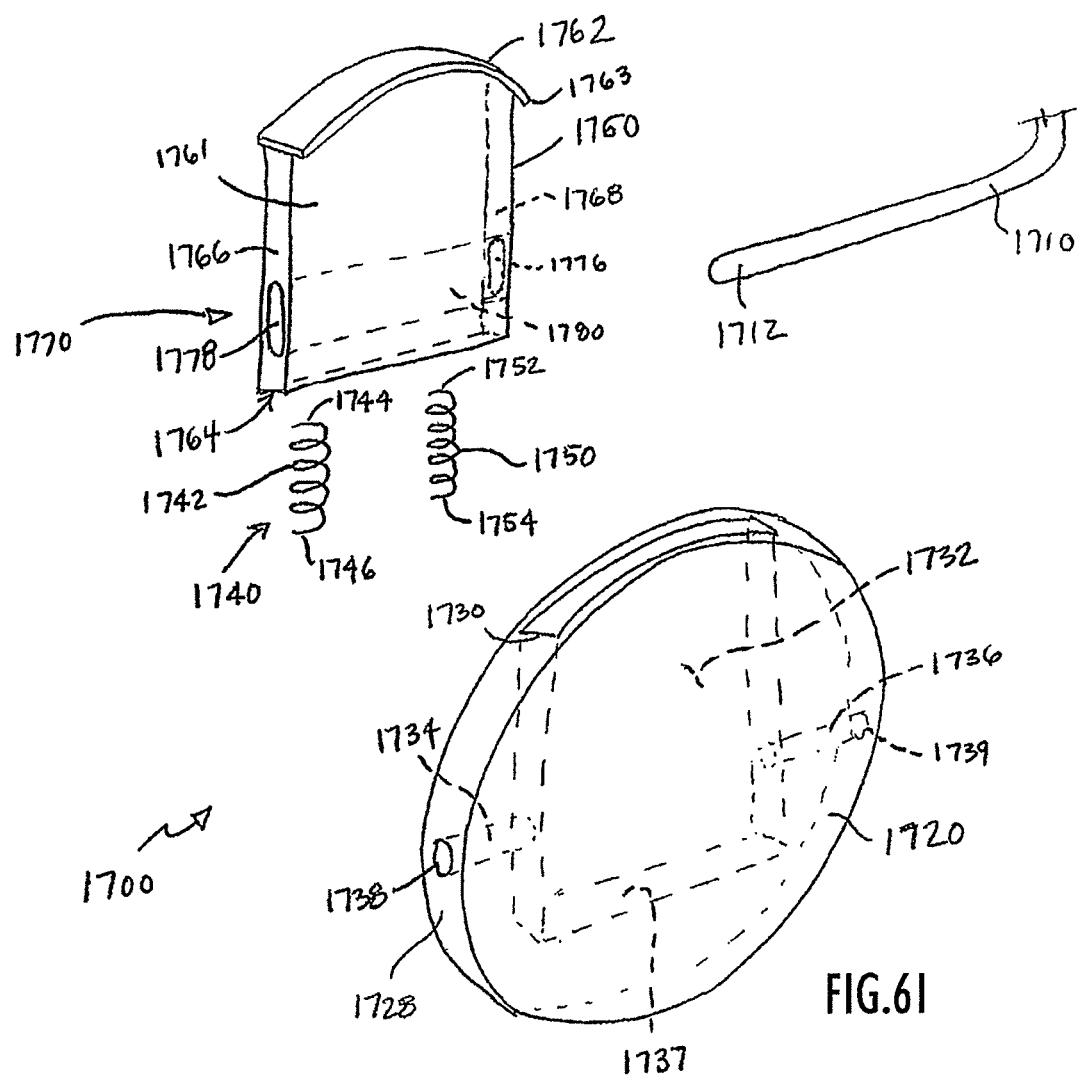
FIG. 61 is an exploded perspective view of the ear protection device components illustrated in FIG. 59.

An alternative embodiment of a frame for an ear protection device is illustrated in FIGS. 59-61. In this embodiment, the frame 1700 includes a band 1710 and two ear frame members or portions. While only ear frame portion 1720 is illustrated and described, the other ear frame portion has a substantially similar structure. Band 1710 is formed from a single piece of material that has two opposite ends (only end 1712 is shown).

The ear frame portion 1720 is movably mounted onto the band 1710 and can be moved along the directions of arrows "AJ" and "AK" as described in greater detail below. Ear frame portion 1720 includes a body 1722 with an inner side 1726 that is proximate to a user's head and an opposite outer side 1724. In this embodiment, the body 1722 is substantially disk-shaped. In alternative embodiments, the body of the ear frame portion can have a different shape.

Referring to FIG. 61, the structure of the body 1722 of the ear frame portion 1720 is illustrated in greater detail. As shown, body 1722 includes an outer perimeter 1728 that has an opening 1730 formed in a portion thereof. The body 1722 includes a chamber or receptacle 1732 that is in communication with the opening 1730. In this embodiment, the chamber 1732 has a substantially rectangular shape and a bottom surface 1737.

On opposite sides of the chamber 1732 are channels 1734 and 1736 that are in communication with the chamber 1732 and extend outwardly toward the outer perimeter 1728. Channel 1734 terminates at an opening 1738 that is formed in the outer perimeter 1728. Similarly, channel 1736 terminates at an opening 1739 that is formed in the outer perimeter 1728.

Also shown in FIG. 61 is an actuator 1760 that is used with the body 1722 of the ear frame portion 1720. In this embodiment, the actuator 1760 includes an actuating portion 1762 and a retaining portion 1770. The actuator 1760 has a generally rectangular-shaped configuration.

The actuator 1760 includes a body 1761 and a plate 1763 coupled to its upper surface and an opposite lower surface 1764. The body 1761 also includes opposite end surfaces 1766 and 1768, each of which includes an opening 1776 and 1778. The openings 1776 and 1778 are in communication with a channel 1780 that extends through the body 1761 from end 1766 to end 1768.

As illustrated in FIGS. 59 and 60, the actuator 1760 is insertable into the opening 1730 of the ear frame portion 1720. The extent to which the actuator 1760 can be inserted into the opening 1730 and chamber 1732 is limited by the plate 1763 on the upper end of the body 1761 of the actuator 1760. After the body 1761 is inserted into the chamber 1732, the plate 1763 contacts the outer perimeter 1728 of the ear frame portion 1720.

A biasing mechanism 1740, in this embodiment—a pair of springs 1742 and 1750, is disposed within the chamber 1732 and beneath the actuator 1760. In this implementation, spring 1742 includes a first end 1744 that engages the lower surface 1764 of the actuator body 1761 and a second end 1746 that engages the lower surface 1737 of the chamber 1732. Similarly, spring 1750 includes a first end 1752 that engages the lower surface 1764 of the actuator body 1761 and a second end 1754 that engages the lower surface 1737 of the chamber 1732. Referring to FIG. 60, the springs 1742 and 1750 exert a force on the lower surface 1764 of the actuator body 1761 along the direction of arrow "AL," thereby tending to push the actuator body 1761 out of the chamber 1732. A user can exert a force on the actuator 1760 along the direction of arrow "AM" to move the actuator body 1761 into the chamber against the forces of the springs 1742 and 1750.

When the user inserts the actuator 1760 into the ear frame portion 1720, the user presses on the actuating portion 1762 along the direction of arrow "AM." At that point, the end 1712 of the band 1710 can be inserted through opening 1730 on the ear frame portion, through channel 1736, into chamber 1732, through opening 1776 on the actuator body 1761, through channel 1780, through opening 1778, through channel 1734 and finally through opening 1738. When the user reduces the pressure applied to the actuating portion 1762, the springs 1742 and 1750 force the actuator body 1761 along the direction of arrow "AL." At that time, the lower surface of the channel 1780 engages the portion of the band 1710 that extends through the channel 1780. That contact, coupled with the positioning of the band 1710 in the channels 1734 and 1736, provides sufficient retaining or clamping force on the band 1710 and as a result, movement of the band 1710 relative to the ear frame portion 1720 is prevented.

To move the ear frame portion 1720 along the band 1710, a user presses on the actuating portion 1762 of the actuator 1760 along the direction of arrow "AM." Movement of the actuator 1760 in that direction causes the lower surface of the channel 1780 to disengage from and no longer contact the band 1710 passing through the channel 1780. At this point, the band 1710 can be moved along the direction of either arrow "AJ" or arrow "AK" through channels 1734 and 1736 and openings 1738 and 1739. The size of channel 1778 in the actuator body 1761 is different than the sizes of channels 1734 and 1736. In particular, channel 1778 is bigger, thereby allowing for relative movement of the actuator body 1761 while the band 1710 still extends through the channel 1778.

In an alternative embodiment, a single spring can be used as the biasing mechanism. In another embodiment, a force exerting structure other than a spring can be used.

Figure 62:
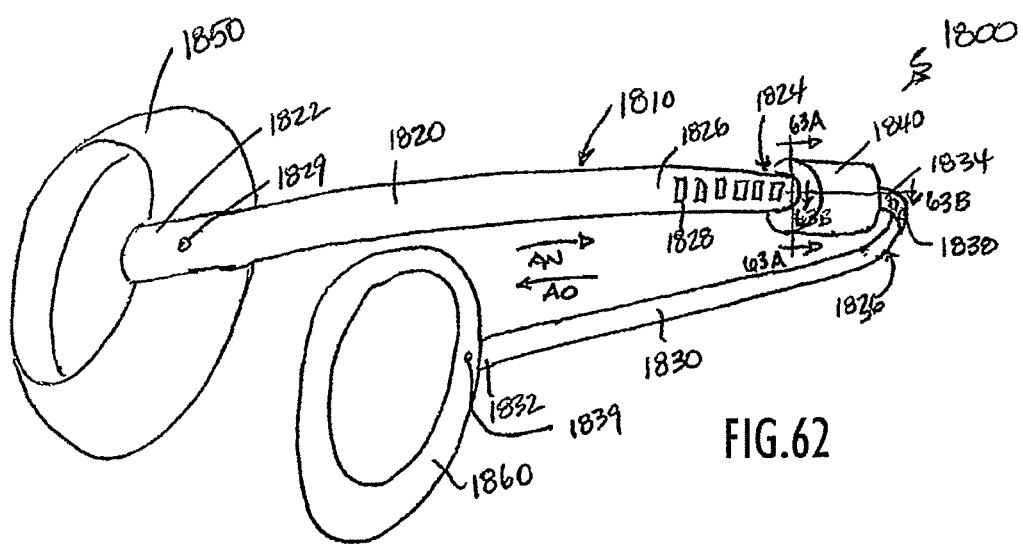
FIG. 62 is a side perspective view of an alternative embodiment of an ear protection device according to the invention.
Figure 63A:
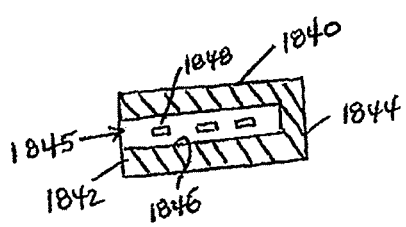
FIG. 63A is a cross-sectional side view of the coupler of the ear protection device illustrated in FIG. 62.
Figure 63B:
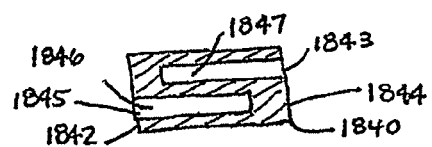
FIG. 63B is a cross-sectional top view of the coupler of the ear protection device illustrated in FIG. 62.
Figure 64:
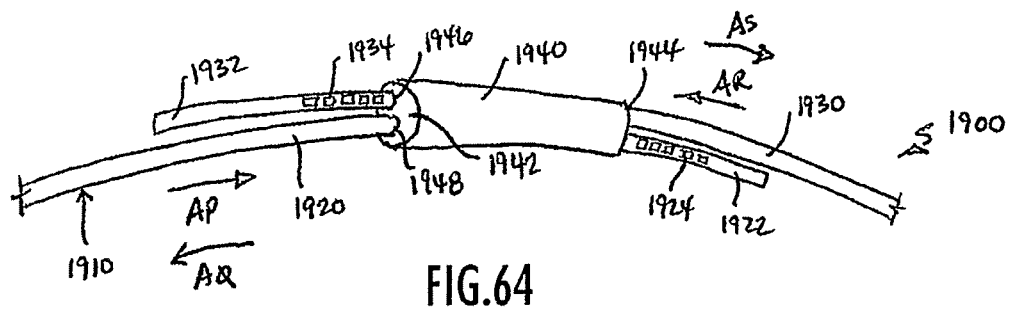
FIG. 64 is a perspective view of some components of an alternative embodiment of an ear protection device according to the invention.
Figure 65:
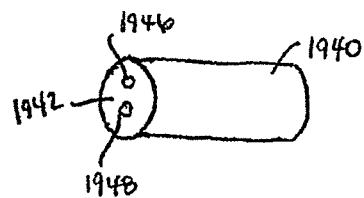
FIG. 65 is a perspective view of the coupler of the ear protection device illustrated in FIG. 64.
Figure 66:
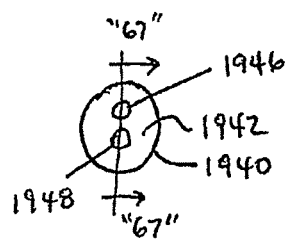
FIG. 66 is an end view of the coupler illustrated in FIG. 64.
Figure 67:
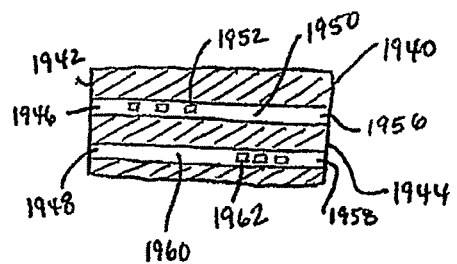
FIG. 67 is a side cross-sectional view of the coupler illustrated in FIG. 66 taken along line "67-67."

An alternative embodiment of a frame for an ear protection device is illustrated in FIGS. 62, 63A and 63B. In this embodiment, the frame 1800 includes a band 1810 and ear frame members or portions 1850 and 1860. Band 1810 includes a first band portion 1820 and a second band portion 1830 that are coupled to each other via coupler 1840. As described below, the coupler 1840 allows the first band portion 1820 and the second band portion 1830 to move relative to each other.

Band portion 1820 includes opposite ends 1822 and 1824 and an outer surface 1826. In this embodiment, the outer surface 1826 includes several protrusions or projections 1828 along a portion of the surface 1826. Similarly, band portion 1830 has opposite ends 1832 and 1834 and an outer surface 1836. The outer surface 1836 includes several protrusions or projections 1838 along a portion of the surface 1836.

Ear frame portion 1850 is coupled to band end 1822 via a connector 1829 such as a rivet or screw. Similarly, ear frame portion 1860 is coupled to band end 1832 via a connector 1839 such as a rivet or screw. In alternative embodiments, connectors 1829 and 1839 can be integrally molded projections extending from the particular ear frame portion and through an opening formed in the respective band end.

Two cross-sectional views of the coupler 1840 are illustrated in FIGS. 63A and 63B. FIG. 63A illustrates a vertical cross-sectional view taken along the line 63A in FIG. 62. FIG. 63B illustrates a horizontal cross-sectional view taken along the line 63B in FIG. 62.

Referring to FIG. 63B, the coupler 1840 has opposite ends 1842 and 1844 and in this embodiment is substantially cylindrical in shape. The coupler 1840 includes an opening 1843 and a channel 1847 in communication with the opening 1843. The coupler 1840 also includes an opening 1845 and a channel 1846 in communication with the opening 1845. The openings 1843 and 1845 are formed in different ends of the coupler 1840 and are configured to receive band end 1834 and band end 1824, respectively. In one embodiment, the band ends 1834 and 1824 are frictionally retained within the coupler 1840. The coupler 1840 can be made of a plastic or rubber material. Alternatively, any material with sufficient structure can be used.

Referring to FIG. 63A, the coupler 1840 can include a series of recesses 1848 along the inner surface of the channel 1846. Channel 1847 may include a similar series of recesses (not shown). Recesses 1848 are configured to receive one or more protrusions 1828 on band portion 1820 when band end 1824 is inserted into the channel 1846. The engagement of protrusions and recesses enable the band portion 1820 to be disposed in several different positions relative to the coupler 1840.

To lengthen the frame 1800, the band portion 1820 can be moved with respect to the coupler 1840 along the direction of arrow "AO" in FIG. 62. The protrusions 1828 on band portion 1820 will engage different recesses 1848 on the coupler 1840. To shorten the overall length of the frame 1800, the band portion 1820 is moved along the direction of arrow "AN" relative to the coupler 1840. The other band portion 1830 can be similarly adjusted relative to the coupler 1840 to shorten or lengthen the overall band 1810.

An alternative embodiment of a frame for an ear protection device is illustrated in FIGS. 64-67. In this embodiment, the frame 1900 includes a band 1910 and two ear frame portions coupled to the band 1910. With respect to this embodiment, the two ear frame portions are not illustrated, but can be similar in structure to ear frame portions 1850 and 1860 described with respect to FIG. 62. Also, the ear frame portions can be coupled to the band 1910 in a manner similar to how ear frame portions 1850 and 1860 are coupled to band 1810.

Band 1910 includes a first band portion 1920 with an end 1922 and several projections or protrusions 1924 along an outer surface of the band portion 1920. Band 1910 also includes a second band portion 1930 with an end 1932 and several projections or protrusions 1934 along an outer surface of the band portion 1930.

The first band portion 1920 and the second band portion 1930 are movably coupled to coupler 1940. In this embodiment, coupler 1940 has a substantially cylindrical configuration with ends 1942 and 1944. Coupler 1940 has two channels 1950 and 1960 (see FIG. 67) that extend from end 1942 to end 1944. Channel 1950 extends between opening 1946 and opening 1956. Similarly, channel 1960 extends between opening 1948 and opening 1958. Channels 1950 and 1960 include several recesses 1952 and 1962, respectively. Recesses 1952 are configured to receive one or more of the projections 1934 on the band portion 1930 as the band portion 1930 is inserted into channel 1950. Similarly, recesses 1962 are configured to receive one or more of the projections 1924 on the band portion 1920 as the band portion 1920 is inserted into channel 1960. Along with frictional forces between engaging surfaces of the band portions and the coupler channels, the recesses and cooperating projections function to retain the band portions in particular positions with respect to the coupler.

To lengthen the band 1910, band portion 1920 can be moved with respect to coupler 1940 along the direction of arrow "AQ." Alternatively, band portion 1930 can be moved with respect to coupler 1940 along the direction of arrow "AS." To shorten the length of the band 1910, band portion 1920 can be moved with respect to coupler 1940 along the direction of arrow "AP." Also, band portion 1930 can be moved with respect to coupler 1940 along the direction of arrow "AR." Band portions 1920 and 1930 can be moved simultaneously or independently. Moreover, band portions 1920 and 1930 can be moved either the same distance or a different distance with respect to the coupler 1940.

Figure 68:
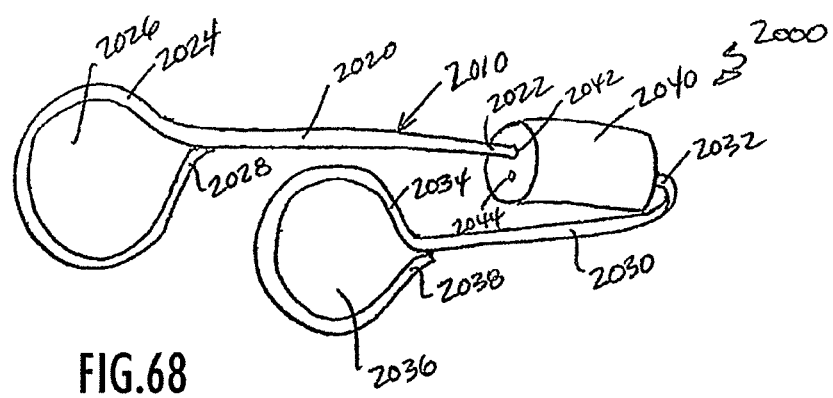
FIG. 68 is a perspective view of an alternative embodiment of an ear protection device according to the invention.

An alternative embodiment of a frame for an ear protection device is illustrated in FIG. 68. In this embodiment, the frame 2000 includes a band 2010. The band 2010 includes a first band portion or member 2020 with a coupling portion 2022 and an engaging portion 2024. The band 2010 also includes a second band portion or member 2030 with a coupling portion 2032 and an engaging portion 2034.

As shown in FIG. 68, band member 2020 is a one piece member that has a portion that is curved to form the engaging portion 2024, which functions similarly to an ear frame portion or member such as those previously described. The engaging portion 2024 is the part of the band member 2020 that is disposed proximate to the user's head when the ear protection device is worn by the user. The engaging portion 2024 defines an opening 2026 that is substantially circularly shaped and closed by end 2028 which is disposed proximate to the main part of the band member 2020.

Similarly, band member 2030 is a one piece member that has a portion that is curved to form the engaging portion 2034, which functions similarly to an ear frame portion or member such as those previously described. The engaging portion 2034 is the part of the band member 2030 that is disposed proximate to the user's head when the ear protection device is worn by the user. The engaging portion 2034 defines an opening 2036 that is substantially circularly shaped and closed by end 2038 which is disposed proximate to the main part of the band member 2030. In alternative embodiments, the engaging portions 2024 and 2034 can have shapes or configurations other than the substantially circular shapes or configurations illustrated in FIG. 68.

In this embodiment, the first band member 2020 and the second band member 2030 engage coupler 2040. Coupler 2040 includes two internal channels that extend through the body of the coupler 2040. As illustrated, the coupling portion 2022 of the band portion 2020 is inserted into opening 2042 of the coupler 2040. Similarly, the coupling portion 2032 of the band portion 2030 is inserted into an opening of the coupler 2040 and can extend through the coupler 2040 and out opening 2044.

In this embodiment, band members 2020 and 2030 are made of metal and the coupler 2040 is made of a rubber-like material. The high frictional forces between the outer surfaces of the band members 2020 and 2030 and the inner surfaces of the coupler 2040 defining the channels retain the band members 2020 and 2030 in particular positions with respect to the coupler 2040. A user can adjust the overall length of the frame 2000 by moving or both of the band members 2020 and 2030 relative to the coupler 2040.

Figure 69:
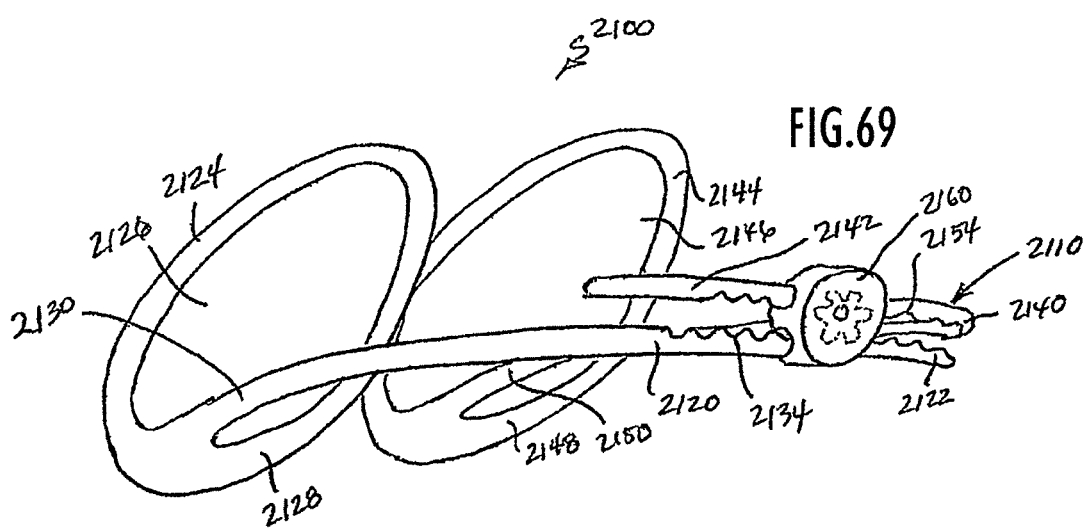
FIG. 69 is a perspective view of an alternative embodiment of an ear protection device according to the invention.
Figure 70:
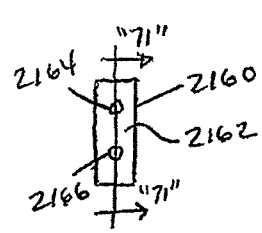
FIG. 70 is an end view of the coupler of the ear protection device illustrated in FIG. 69.
Figure 71:
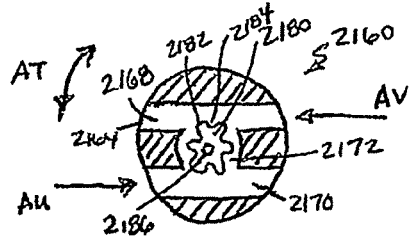
FIG. 71 is a cross-sectional side view of the coupler illustrated in FIG. 70, taken along the line "71-71."

An alternative embodiment of a frame for an ear protection device is illustrated in FIGS. 69-71. In this embodiment, the frame 2100 has a band 2110 that includes a first band member 2120 and a second band member 2140.

Band member 2120 has a first end 2122 and an opposite second end 2130. Band member 2120 between the first end 2122 and the second end 2130 has a generally curved configuration. Band member 2120 includes an engaging portion 2124 coupled to end 2130. The engaging portion 2124 is configured to be disposed proximate to a user's head when the user is wearing the ear protection device. In this embodiment, engaging portion 2124 is substantially circular, but in other embodiments, the engaging portion can have any shape or configuration.

The engaging portion 2124 includes an outer member 2128 that defines an opening 2126. The end 2130 of the band member 2120 approaches the outer member 2128 at an angle and offset from the side of the outer member 2128. Also, the end 2130 is coupled proximate to a lower end of the outer member 2128. Band member 2120 also includes several recesses 2134 formed in a surface as shown in FIG. 69.

Band member 2140 has a first end 2142 and an opposite second end 2150. Band member 2140 between the first end 2142 and the second end 2150 has a generally curved configuration. Band member 2140 includes an engaging portion 2144 coupled to end 2150. The engaging portion 2144 is configured to be disposed proximate to a user's head when the user is wearing the ear protection device. In this embodiment, engaging portion 2144 is substantially circular, but in other embodiments, the engaging portion can have any shape or configuration.

The engaging portion 2144 includes an outer member 2148 that defines an opening 2146. The end 2150 of the band member 2140 approaches the outer member 2148 at an angle and offset from the side of the outer member 2148. Also, the end 2150 is coupled proximate to a lower end of the outer member 2148. Band member 2140 also includes several recesses 2154 formed in a surface as shown in FIG. 69.

In this embodiment, the frame 2100 includes a coupler 2160. Coupler 2160 has an outer surface 2162 with opening 2164 and 2166 formed therein. Referring to FIG. 71, channels 2168 and 2170 extend through the coupler 2160 from one side to the other side. Also, the coupler 2160 includes a central area 2172 in which a coupling member 2180 is disposed. Coupling member 2180 is rotatably mounted on a post 2186 and movable along the directions of arrow "AT" (see FIG. 71). Coupling member 2180 includes several teeth 2182 between which recesses 2184 are located.

Channel 2170 is configured to receive end 2122 of band member 2120. As end 2122 is inserted into and through channel 2170 along the direction of arrow "AU," recesses 2134 on band member 2120 are engaged by teeth 2182 on the coupling member 2180. Channel 2168 is configured to receive end 2142 of band member 2140. As end 2142 is inserted into and through channel 2168 along the direction of arrow "AV," recesses 2154 on band member 2140 are engaged by teeth 2182 on the coupling member 2180. Movement of either band member 2120 or band member 2140 in a first direction relative to the coupler 2160, causes movement of the coupling member 2180 and thereby causes movement of the other band member 2120 or band member 2140 in an opposite direction. To remove the band members 2120 and 2140 from the coupler 2160, the user moves one of the band members 2120 and 2140 in a direction away from the coupler 2160 and the other band member is simultaneously moved out of engagement with the coupler 2160.

Figure 72:
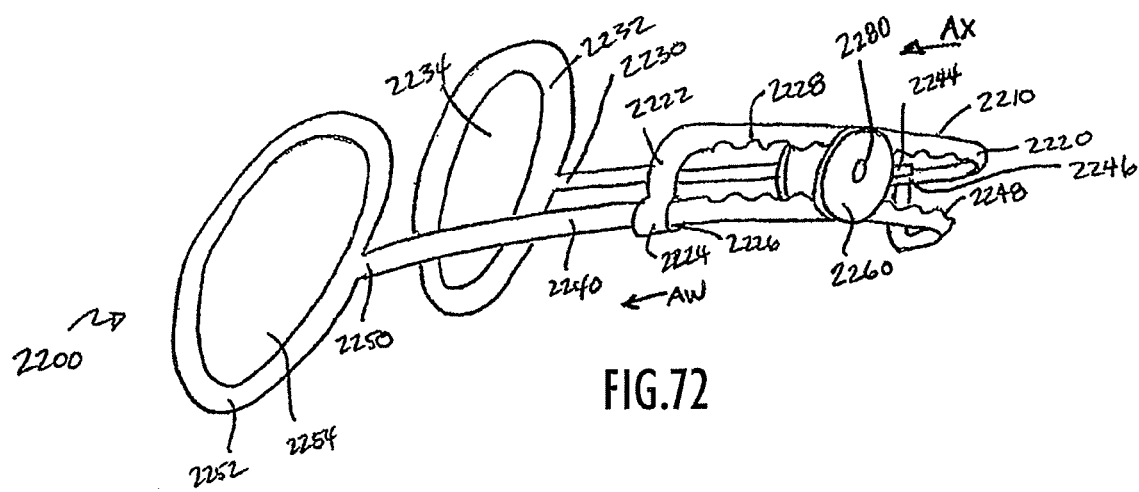
FIG. 72 is a perspective view of an alternative embodiment of an ear protection device according to the invention.
Figure 73:
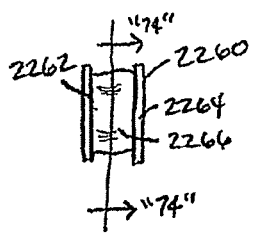
FIG. 73 is an end view of the coupler of the ear protection device illustrated in FIG. 72.
Figure 74:
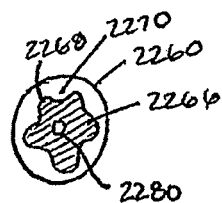
FIG. 74 is a cross-sectional side view of the coupler illustrated in FIG. 73, taken along line "74-74."

An alternative embodiment of a frame for an ear protection device is illustrated in FIGS. 72-74. In this embodiment, the frame 2200 includes a band 2210 and a coupler 2260. Band 2210 includes a first band portion 2220 and a second band portion 2240. The first band portion 2220 and the second band portion 2240 are coupled together and can move relative to each other to change the overall length of the frame 2200.

In this embodiment, band portion 2220 has a substantially curved configuration from end 2222 to end 2230. The band portion 2220 includes an engaging portion 2232 that defines an opening 2234 and a coupling portion 2224 that is coupleable to the other band portion 2240. Coupling portion 2224 includes a passageway 2226 into which part of band portion 2240 can be inserted. The end of the coupling portion 2224 can be wrapped around the band portion 2240 to couple the end of the first band portion 2220 to the second band portion 2240. In one embodiment, the coupling portion 2224 can be snapped onto the second band portion 2240. Band portion 2220 includes several recesses 2228 formed in a surface of the band portion 2220. The function of the recesses 2228 is described in detail below.

Band portion 2240 has a substantially curved configuration from end 2242 to end 2250. The band portion 2240 includes an engaging portion 2252 that defines an opening 2254 and a coupling portion 2244 that is coupleable to the other band portion 2220. Coupling portion 2244 includes a passageway 2246 into which part of band portion 2220 can be inserted. The end of the coupling portion 2244 can be wrapped around the band portion 2220 to couple the end of the second band portion 2240 to the first band portion 2220. In one embodiment, the coupling portion 2244 can be snapped onto the first band portion 2220. Band portion 2240 includes several recesses 2248 formed in a surface of the band portion 2240. The function of the recesses 2248 is described in detail below.

The overall length of the frame 2200 can be adjusted by moving the first band portion 2220 and the second band portion 2240 relative to each other. To shorten the length, engaging portion 2232 and engaging portion 2252 are moved toward each other. During that movement, the coupling portion 2224 of the first band portion 2220 slides along the second band portion 2240 along the direction of arrow "AW" (see FIG. 72) and the coupling portion 2244 of the second band portion 2240 slides along the first band portion 2220 along the direction of arrow "AX" (see FIG. 72). The coupling portions 2224 and 2244 keep the band portions 2220 and 2240 coupled together.

The structure and function of coupler 2260 is now described. In this embodiment, the coupler 2260 is disposed between the band portions 2220 and 2240 prior to both coupling portions 2224 and 2244 being connected. Coupler 2260 has outer plates 2262 and 2264 and an engaging portion 2266 disposed between the outer plates 2262 and 2264 and rotatably mounted on a center post 2280.

As illustrated in FIG. 74, the engaging portion 2266 includes several teeth 2268 that are defined by recesses 2270 therebetween. The teeth 2268 are configured to engage recesses 2228 on band portion 2220 and recesses 2248 on band portion 2240.

As one of the band portions 2220 and 2240 are moved in a direction, the engaging portion 2266 of the coupler 2260 moves as well as the other band portion. The movement of the engaging portion 2266 of the coupler 2260 depends on the movement of one of the band portions. To decouple the components of the frame 2200, the second band portion 2240 is removed from the coupling portion 2224 of the first band portion 2220 and the first band portion 2220 is removed from the coupling portion 2244 of the second band portion 2240.

Figure 75:
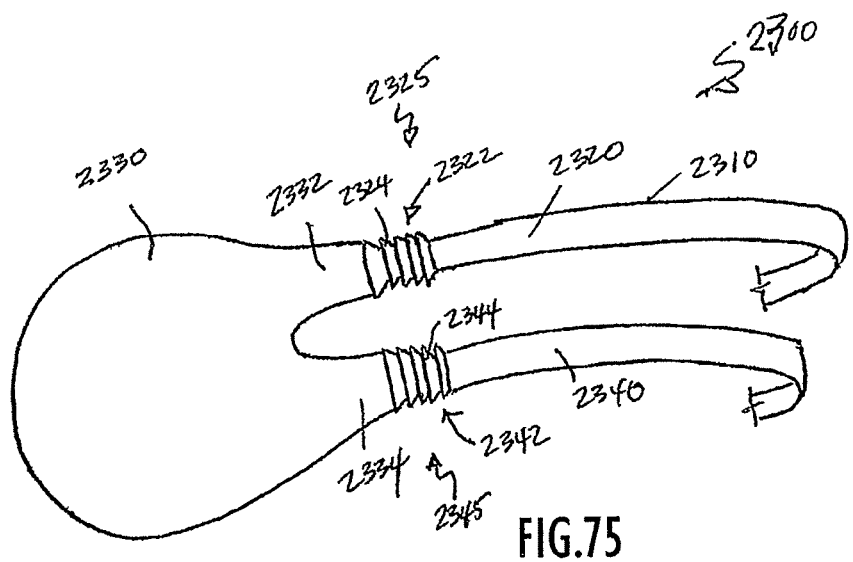
FIG. 75 is a perspective view of an alternative embodiment of an ear protection device according to the invention.
Figure 76:
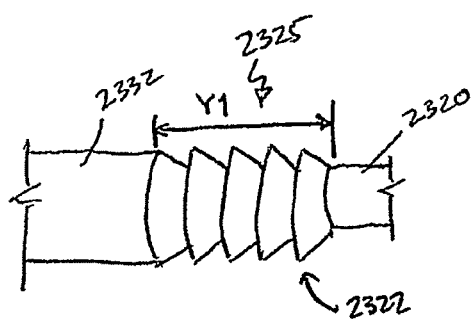
FIG. 76 is a partial side view of the extending portion of the ear protection device in a collapsed configuration.
Figure 77:
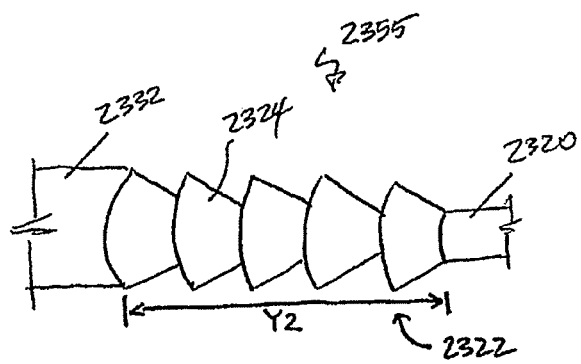
FIG. 77 is a partial side view of the extending portion of the ear protection device in an extended configuration.

An alternative embodiment of a frame for an ear protection device is illustrated in FIGS. 75-77. In this embodiment, the frame 2300 includes a band 2310 that is integrally formed. The band 2310 is substantially curved along most of its length. The band 2310 includes a first band portion 2320 and a second band portion 2340 that form the middle portion of the frame 2300. Band portions 2320 and 2340 are substantially parallel.

The band 2310 includes an engaging portion 2330 at one end and another engaging portion (not shown) at its other end. Engaging portion 2330 is configured to be disposed proximate to a user's head. Engaging portion 2330 includes coupling portions 2332 and 2334.

The band 2310 also includes an extending portion 2322 that is located between an end of band portion 2320 and the coupling portion 2332 of engaging portion 2330. Similarly, band 2310 includes an extending portion 2342 that is located between an end of band portion 2340 and the coupling portion 2334 of engaging portion 2330. As illustrated in FIG. 75, extending portion 2322 includes several pleats 2324 that can be expanded and contracted to vary the overall length of the extending portion 2322. Similarly, extending portion 2342 includes several pleats 2424 that can be expanded and contracted to vary the overall length of the extending portion 2342. In FIG. 75, each of the extending portions 2322 and 2342 is disposed in collapsed configurations 2325 and 2345, respectively.

Referring to FIG. 76, an enlarged view of a collapsed configuration 2325 of the extending portion 2322 is illustrated. In this configuration 2325, the end of the coupling portion 2332 and the end of band portion 2320 are spaced apart by a distance Y1. This configuration is achieved by moving the coupling portion 2332 along the direction of arrow "AY" and by moving the band portion 2320 along the direction of arrow "AZ." Such movements cause the pleats 2324 in the extending portion 2322 to fold on themselves and thereby reduce the length of the extending portion 2322.

Referring to FIG. 77, an enlarged view of an extended configuration 2355 of the extending portion 2324 is illustrated. In this configuration 2355, the end of the coupling portion 2332 and the end of the band portion 2320 are spaced apart by a distance Y2. This configuration is achieved by moving the coupling portion 2322 along the direction of arrow "BA" and by moving the band portion 2320 along the direction of arrow "BB." Such movements cause the pleats 2324 in the extending portion 2322 to expand and pull apart from each other and thereby increase the length of the extending portion 2322.

The adjustments of extending portions 2322 and 2342 occur simultaneously and change the overall length of the band 2310. The other ends of the band portions 2320 and 2340 include similar extending portions that enable further adjustment of the length of the band 2310. The more pleats that are included to form an extending portion, the greater the range of adjustability of the length of the band.

Figure 78:
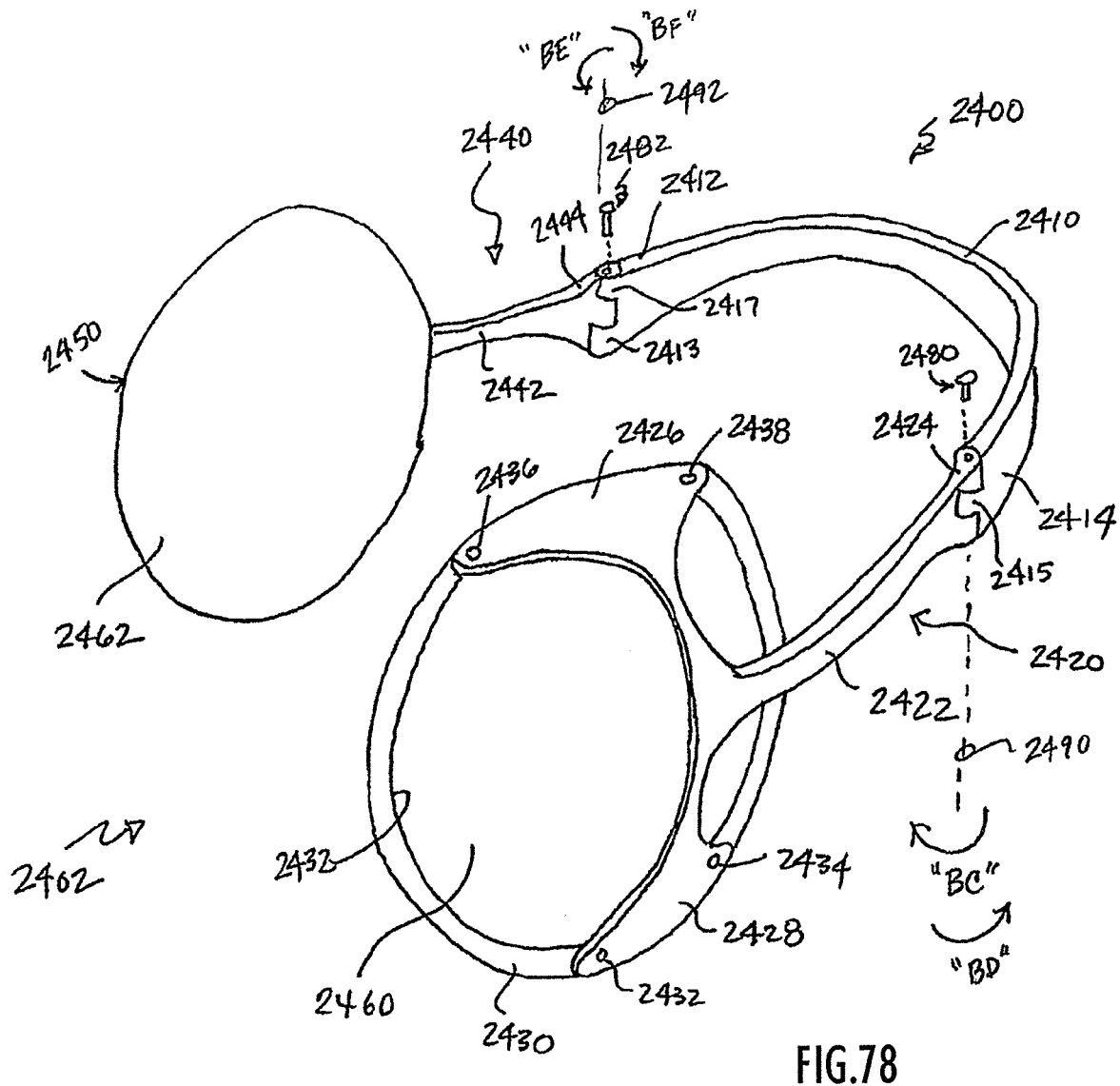
FIG. 78 is a perspective view of an alternative embodiment of a frame for an ear protection device according to the invention in a deployed configuration.
Figure 79:
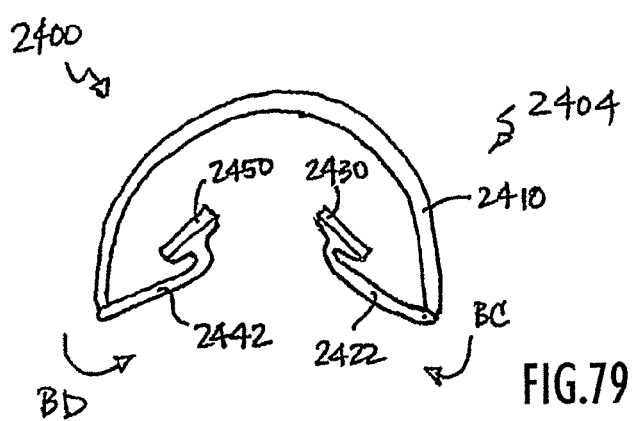
FIG. 79 is a top view of the frame illustrated in FIG. 78 in a collapsed configuration.

An alternative embodiment of a frame for an ear protection device is illustrated in FIGS. 78 and 79. In this embodiment, the frame 2400 includes a band 2410 and ear frame members 2420 and 2440. The ear frame members 2420 and 2440 are movable relative to the band 2410 so that the frame 2400 and the ear protection device can be disposed in either a deployed configuration 2402 (see FIG. 78) or a collapsed configuration 2404 (see FIG. 79).

The band 2410 includes a first end 2412 and an opposite second end 2414. Ear frame member 2440 is coupled to the first end 2412 of the band 2410 and ear frame member 2420 is coupled to the second end 2414 of the band 2410. Proximate to end 2412 are two portions 2413 and 2417 that are used to couple the band end 2412 and the ear frame member 2440. Similarly, proximate to end 2414 is a portion 2415 that is used to couple the band end 2414 and the ear frame member 2420. A connector 2480, such as a screw or rivet, is used to couple end 2424 of ear frame member 2420 to band end 2414. Similarly, a connector 2482, such as a screw or rivet, is used to couple end 2444 of ear frame member 2440 to band end 2412.

Accordingly, ear frame member 2420 is movable about a pivot axis 2490 between a deployed position (see FIG. 78) and a collapsed position (see FIG. 79). In particular, the ear frame member 2420 is movable about axis 2490 along the direction of arrow "BC" to move from its deployed position to its collapsed position, and along the direction of arrow "BD" to move from its collapsed position to its deployed position. Similarly, ear frame member 2440 is movably about a pivot axis 2492 between a deployed position (see FIG. 78) and a collapsed position (see FIG. 79). In particular, the ear frame member 2440 is movable about axis 2492 along the direction of arrow "BE" to move from its deployed position to its collapsed position and along the direction of arrow "BF" to move from its collapsed position to its deployed position.

Ear frame member 2420 includes a frame 2430 that is substantially circular in shape. In other embodiments, the frame can have a different shape or configuration. In this embodiment, the ear frame member 2420 has a fabric member 2460 that is coupled to the frame 2430. The fabric member 2460 can be fixedly coupled to the frame 2430. For example, the fabric member 2460 can be adhered to the frame 2430 using any conventional technique. Alternatively, fabric member 2460 can be removably coupled to the frame 2430 using a resilient border that can be stretched out and over the ring 2430.

Ear frame member 2420 includes an arm 2422 that has ends 2426 and 2428 that are coupled to the frame 2430 by connectors 2432, 2434, 2436, and 2438. The arm 2422 structure provides the application of force to the frame 2430 at multiple locations and in a spread apart manner and uses minimal material. In alternative embodiments, the arm can have any shape or configuration.

Ear frame member 2440 includes an arm 2442 with an end 2444 and a frame 2450 to which a fabric material 2462 is coupled.

The terms "ear frame portion" and "ear frame member" are used herein in reference to a portion of an ear protection device that is disposed proximate to a user's head when the ear protection device is worn by the user. In various embodiments, the components of the frames disclosed herein can be molded plastic parts, including Crastin, metallic parts, rubber parts, or any similar structure that can provide sufficient rigidity and strength for the intended function of the components.

Various fabric shells can be used. A one piece membrane can be sewn around a frame to define an interior in which all or part of a frame can be disposed. Alternatively, two membranes can be coupled together to form a shell with an interior in which all or part of a frame can be disposed. In other embodiments, three or more membranes can be provided and coupled together to form a shell with an interior in which all or a portion of a frame can be disposed.

In other embodiments, separate fabric portions can be coupled to the ear frame portions or members only, thereby leaving the remainder of the frame, including the band, uncovered. For example, fabric portions can be coupled to the inner surface of the ear frame portions or members to provide cushioning and comfort to the user.

In various embodiments, the bands or band portions or members can have an increased thickness section that provides additional support to the frame. For example, the middle portion of a frame can have a larger cross-sectional area than the distal or end portions to which ear frame members are connected. The larger cross-sectional area increases the strength of the band and thereby improves the ability of the ear protection device to stay on a user's head.

In various embodiments, some of the components of the ear protection device frame can be slidably, rotatably or otherwise movably connected to other components.

In some embodiments, parts that are formed separately and subsequently coupled together can be integrally formed, such as by molding.

The opening in an ear frame member or portion can be provided for several reasons, including less material, lighter weight of the ear frame member, better hearing than if it did not include an opening, and/or a better distribution of force on the user's head.

The disclosures of the following U.S. patents are hereby incorporated by reference in their entirety for all purposes: U.S. Pat. Nos. 5,835,609, 6,332,223, 6,499,146, 6,502,247, 6,502,248, 6,735,784, 6,880,174, 6,920,645, and 6,978,483.

While the invention has been described in detail and with references to specific embodiments thereof, it will be apparent to one skilled in the art that various changes and modifications can be made therein without departing from the spirit and scope thereof. Thus, it is intended that the present invention covers the modifications and variations of this invention.

What is claimed is:

1. A frame for an ear protection device, the frame being configured to extend around the back of a user's head, comprising:
   a band;
   a first ear frame portion, the first ear frame portion being movably coupled to the band to allow adjustment of the first ear frame portion relative to the band, the first ear frame portion including:
      a first body defining a first channel through which a portion of the band is inserted; and
      a first actuator defining a second channel through which a portion of the band is inserted, the first actuator being configured to be coupled to the first body, the first actuator having a first position and a second position,
   when the first actuator is in the first position, the first ear frame portion coupled to and not moveable relative to the band,
   when the first actuator is in the second position, the second channel is aligned with the first channel such that the first ear frame portion is configured to be coupled to and moveable relative to the band; and
   a second ear frame portion, the second ear frame portion being movably coupled to the band to allow adjustment of the second ear frame portion relative to the band, the second ear frame portion including:
      a second body; and
      a second actuator, the second actuator being configured to be coupled to the second body and movable relative thereto, the second actuator being engageable with the band to removably couple the second ear frame portion to the band.

2. The frame of claim 1, wherein the band includes two opposite ends, the first ear frame portion being movably coupled proximate to one end of the band, and the second ear frame portion being movably coupled proximate to the other end of the band.

3. The frame of claim 1, wherein the first ear frame portion is slidable along a portion of the band when the first actuator is in the second position.

4. The frame of claim 3, wherein the first ear frame portion can be slid off the band when the first actuator is in the second position.

5. The frame of claim 1, wherein the first body defines a chamber into which the first actuator is insertable.

6. The frame of claim 1, wherein, when the first actuator is in the first position, the first actuator provides a retaining force on the band and movement of the band relative to the first ear frame portion is prevented.

7. The frame of claim 1, wherein the first actuator is engaged with the band in the first position and disengaged from the band in the second position.

8. A frame for an ear protection device, the frame being configured to extend around the back of a user's head, comprising:
   a band;
   a first ear frame portion, the first ear frame portion being movably coupled to the band to allow adjustment of the first ear frame portion relative to the band, the first ear frame portion including:
      a first body defining a chamber; and
      a first actuator, the first actuator being configured to be insertable into the chamber of the first body and moveable relative thereto, the first actuator being selectively engageable with the band to removable couple the first ear frame portion to the band;
      a biasing mechanism, the biasing mechanism being disposed in the chamber, the biasing mechanism engaging the first actuator and a surface of the chamber; and
   a second ear frame portion, the second ear frame portion being movably coupled to the band to allow adjustment of the second ear frame portion relative to the band, the second ear frame portion including:
      a second body; and
      a second actuator, the second actuator being configured to be coupled to the second body and moveable relative thereto, the second actuator being engageable with the band to removably couple the second ear frame portion to the band.

9. The frame of claim 8, the biasing mechanism being configured to exert a force on the first actuator to tend to disengage the first actuator from the first body.

10. The frame of claim 9, wherein the biasing mechanism includes a spring, the spring being configured to exert a force on the first actuator to push the first actuator out of the chamber.

* * * * *